US009233776B2

(12) United States Patent
Bazala et al.

(10) Patent No.: US 9,233,776 B2
(45) Date of Patent: Jan. 12, 2016

(54) MOLECULAR IMAGING VIAL TRANSPORT CONTAINER AND FLUID INJECTION SYSTEM INTERFACE

(71) Applicant: MEDRAD, INC., Indianola, PA (US)

(72) Inventors: Jason L Bazala, Irwin, PA (US); Ryan C Kaintz, Allison Park, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 219 days.

(21) Appl. No.: 13/800,194

(22) Filed: Mar. 13, 2013

(65) Prior Publication Data

US 2013/0331810 A1  Dec. 12, 2013

Related U.S. Application Data

(60) Provisional application No. 61/656,618, filed on Jun. 7, 2012.

(51) Int. Cl.
*A61J 1/20* (2006.01)
*B65D 17/00* (2006.01)
(Continued)

(52) U.S. Cl.
CPC ............... *B65D 17/00* (2013.01); *A61J 1/1406* (2013.01); *A61J 1/16* (2013.01); *A61J 1/20* (2013.01); *A61J 1/2096* (2013.01); *A61J 1/1418* (2015.05); *A61J 1/201* (2015.05)

(58) Field of Classification Search
CPC ............. A61J 1/16; A61J 1/1406; A61J 1/20; A61J 1/2096; A61J 2001/201; B65D 17/00
See application file for complete search history.

(56) References Cited

U.S. PATENT DOCUMENTS 2,487,728 A   11/1949   Quiring
2,492,326 A   12/1949   Scotti
(Continued)

FOREIGN PATENT DOCUMENTS

EP   0915760 B1   5/2002
EP   1616587 A1   1/2006
(Continued)

OTHER PUBLICATIONS

The International Search Report and Written Opinion mailed on May 28, 2014 from corresponding PCT Application No. PCT/US2013/044031, filed on Jun. 4, 2013.
(Continued)

*Primary Examiner* — Philip R Wiest
*Assistant Examiner* — Benjamin Klein
(74) *Attorney, Agent, or Firm* — Joseph L. Kent; David Schramm; James R. Stevenson

(57) ABSTRACT

A pharmaceutical transport container includes a first body portion adapted to receive at least a portion of a pharmaceutical vial, a second body portion removably engaged with the first body portion to fully enclose the vial, and a flexible ring positioned in an interior cavity of the second body portion and configured to flex between a relaxed state and a radially-outward extended state. The pharmaceutical transport container may also include a removable end cap having a receiving chamber to receive the first body portion, and/or a guide tab extending from an exterior surface of the second body portion to engage a guide slot defined in a fluid injection system docking station, whereby the transport container translates axially and rotationally into the docking station to establish a fluid connection between the vial and a fluid connector mechanism or element disposed within the docking station.

25 Claims, 26 Drawing Sheets

(51) Int. Cl.
*A61J 1/14* (2006.01)
*A61J 1/16* (2006.01)

(56) References Cited

U.S. PATENT DOCUMENTS

| | | |
|---|---|---|
| 2,761,717 A | 9/1956 | Mahlke |
| 2,915,640 A | 12/1959 | Grubel et al. |
| 3,027,034 A | 3/1962 | Christian |
| 3,369,121 A | 2/1968 | Bruno et al. |
| 3,432,666 A | 3/1969 | Geoffrey et al. |
| 3,531,644 A | 9/1970 | Curtis |
| 3,630,403 A | 12/1971 | Robert |
| 3,655,985 A | 4/1972 | Brown et al. |
| 3,673,411 A | 6/1972 | Herman |
| 3,718,138 A | 2/1973 | Alexandrov et al. |
| 3,754,141 A | 8/1973 | Leebl et al. |
| 3,811,591 A | 5/1974 | Novitch |
| 3,850,325 A | 11/1974 | MacLeod |
| 3,882,315 A | 5/1975 | Soldan |
| 3,896,958 A | 7/1975 | Robbins et al. |
| 3,971,955 A | 7/1976 | Heyer et al. |
| 3,973,554 A | 8/1976 | Tipton |
| 3,984,695 A | 10/1976 | Collica et al. |
| 4,074,824 A | 2/1978 | Kontes |
| 4,081,688 A | 3/1978 | Fries |
| 4,084,097 A | 4/1978 | Czaplinski et al. |
| 4,092,546 A | 5/1978 | Larrabee |
| 4,122,836 A | 10/1978 | Burnett |
| 4,307,713 A | 12/1981 | Galkin et al. |
| 4,401,108 A | 8/1983 | Galkin et al. |
| 4,409,966 A | 10/1983 | Lambrecht et al. |
| 4,562,829 A | 1/1986 | Bergner |
| 4,585,009 A | 4/1986 | Barker et al. |
| 4,594,214 A | 6/1986 | Popp et al. |
| 4,673,813 A | 6/1987 | Sanchez |
| 4,738,388 A | 4/1988 | Bienek et al. |
| 5,027,966 A | 7/1991 | Yadock |
| 5,042,679 A | 8/1991 | Crowson et al. |
| 5,274,239 A | 12/1993 | Lane et al. |
| 5,303,836 A | 4/1994 | Childress |
| 5,316,146 A | 5/1994 | Graff |
| 5,437,387 A | 8/1995 | Burns |
| 5,472,403 A | 12/1995 | Cornacchia et al. |
| 5,514,071 A | 5/1996 | Sielaff, Jr. et al. |
| 5,519,931 A | 5/1996 | Reich |
| 5,624,410 A | 4/1997 | Tsukada et al. |
| 5,695,090 A | 12/1997 | Burdick |
| 5,725,114 A | 3/1998 | Pickman |
| 5,817,067 A | 10/1998 | Tsukada |
| 5,828,073 A | 10/1998 | Zhu et al. |
| 5,834,788 A | 11/1998 | Fu et al. |
| 5,857,579 A | 1/1999 | Finneran |
| 5,865,805 A | 2/1999 | Ziemba |
| 5,927,351 A | 7/1999 | Zhu et al. |
| 5,944,190 A | 8/1999 | Edelen |
| 5,993,425 A * | 11/1999 | Kriesel .................. 604/191 |
| 6,162,198 A | 12/2000 | Coffey et al. |
| 6,425,174 B1 | 7/2002 | Reich |
| 6,585,684 B1 | 7/2003 | Hughett et al. |
| 6,586,758 B2 | 7/2003 | Martin |
| 6,589,158 B2 | 7/2003 | Winkler |
| 6,614,040 B1 | 9/2003 | Zens |
| 6,767,319 B2 | 7/2004 | Reilly et al. |
| 6,773,673 B1 | 8/2004 | Layfield et al. |
| 7,040,856 B2 | 5/2006 | Reich |
| 7,086,133 B2 | 8/2006 | Reich |
| 7,105,846 B2 | 9/2006 | Eguchi |
| 7,151,267 B2 | 12/2006 | Lemer |
| 7,170,072 B2 | 1/2007 | Schwarz et al. |
| 7,199,375 B2 | 4/2007 | Drobnik et al. |
| 7,307,265 B2 | 12/2007 | Polsinelli et al. |
| 7,419,478 B1 | 9/2008 | Reilly et al. |
| 7,546,855 B2 | 6/2009 | Rodewald |
| 7,694,610 B2 | 4/2010 | Flores et al. |
| 7,753,835 B2 | 7/2010 | Van Der Lee et al. |
| 7,772,565 B2 | 8/2010 | Wilson |
| 7,812,322 B2 | 10/2010 | Wagner et al. |
| 7,842,023 B2 | 11/2010 | Chinol et al. |
| 7,934,614 B2 | 5/2011 | Finneran |
| 7,975,733 B2 | 7/2011 | Horppu et al. |
| 8,409,165 B2 | 4/2013 | Niedospial, Jr. et al. |
| 8,496,272 B2 | 7/2013 | Davis |
| 8,505,787 B2 | 8/2013 | Fox et al. |
| 8,633,461 B2 | 1/2014 | Fago et al. |
| 2003/0222228 A1 | 12/2003 | Chen Fu et al. |
| 2004/0015038 A1 | 1/2004 | Lemer |
| 2004/0084340 A1 | 5/2004 | Morelle et al. |
| 2004/0254525 A1 | 12/2004 | Uber, et al. |
| 2005/0085682 A1 | 4/2005 | Sasaki et al. |
| 2005/0107698 A1 | 5/2005 | Powers et al. |
| 2005/0203329 A1 | 9/2005 | Muto et al. |
| 2005/0203330 A1 | 9/2005 | Muto et al. |
| 2005/0234424 A1 | 10/2005 | Besing et al. |
| 2005/0247893 A1 | 11/2005 | Fu et al. |
| 2005/0277833 A1 | 12/2005 | Williams |
| 2006/0151048 A1 | 7/2006 | Tochon Danguy et al. |
| 2006/0293553 A1 | 12/2006 | Polsinelli et al. |
| 2007/0034537 A1 | 2/2007 | Fago et al. |
| 2008/0177126 A1 | 7/2008 | Tate et al. |
| 2008/0200747 A1 * | 8/2008 | Wagner et al. .................. 600/5 |
| 2008/0242915 A1 | 10/2008 | Jackson et al. |
| 2010/0019174 A1 | 1/2010 | Helle et al. |
| 2010/0049159 A1 | 2/2010 | Fangrow |
| 2010/0160889 A1 | 6/2010 | Smith et al. |
| 2010/0168712 A1 | 7/2010 | Tuckwell et al. |
| 2010/0185040 A1 | 7/2010 | Uber et al. |
| 2011/0132907 A1 | 6/2011 | Hajichristou et al. |
| 2011/0178359 A1 | 7/2011 | Hirschman et al. |
| 2011/0201867 A1 | 8/2011 | Wagner |
| 2011/0209764 A1 | 9/2011 | Uber et al. |
| 2011/0214781 A1 | 9/2011 | Horppu et al. |
| 2011/0215267 A1 | 9/2011 | Fago et al. |
| 2012/0007004 A1 | 1/2012 | Valentin et al. |
| 2012/0305800 A1 | 12/2012 | Mayfield et al. |
| 2013/0001446 A1 | 1/2013 | Sakashita |
| 2014/0046295 A1 | 2/2014 | Uber, III et al. |
| 2014/0048432 A1 | 2/2014 | Kakiuchi et al. |

FOREIGN PATENT DOCUMENTS

| | | |
|---|---|---|
| EP | 1927996 A2 | 6/2008 |
| JP | 2004290455 A | 10/2004 |
| JP | 2005283431 A | 10/2005 |
| WO | 2004004787 A2 | 1/2004 |
| WO | 2006051531 A2 | 5/2006 |
| WO | 2006124775 A2 | 11/2006 |
| WO | 2007010534 A2 | 1/2007 |
| WO | 2007056654 A1 | 5/2007 |
| WO | 2008083313 A2 | 7/2008 |
| WO | 2009149367 A1 | 12/2009 |
| WO | 2012019201 | 2/2012 |
| WO | WO 2012/019201 * | 2/2012 ............... G01N 1/28 |

OTHER PUBLICATIONS

International Preliminary Report on Patentability for Application No. PCT/US2013/044031, mailed on Dec. 9, 2014, 7 pages.
International Preliminary Report on Patentability for Application No. PCT/US2013/048484, mailed on Dec. 31, 2014, 6 pages.
International Search Report and Written Opinion for Application No. PCT/US2013/048484, mailed on Oct. 22, 2013, 8 pages.
International Search Report and Written Opinion for Application No. PCT/US2014/022448, mailed on Jul. 15, 2014, 8 pages.

* cited by examiner

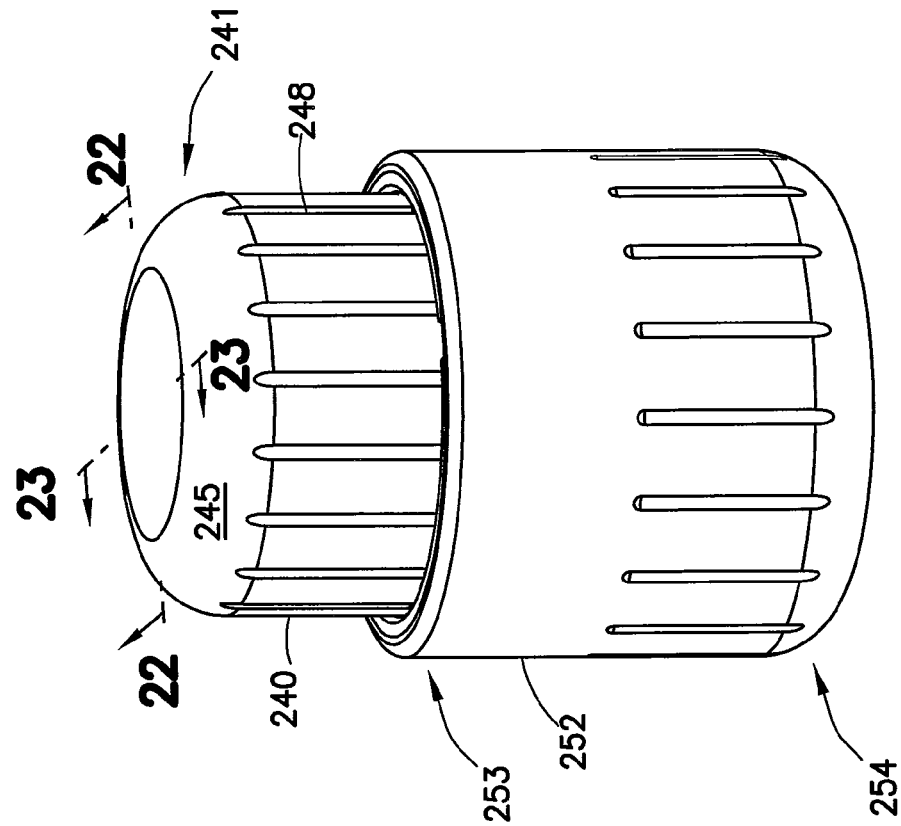
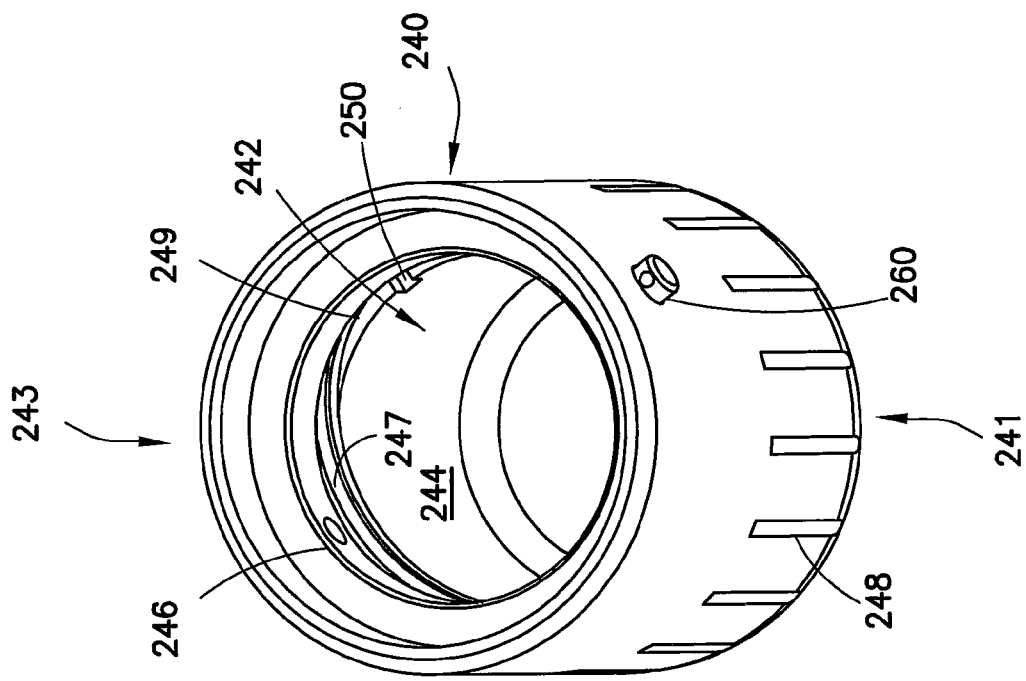

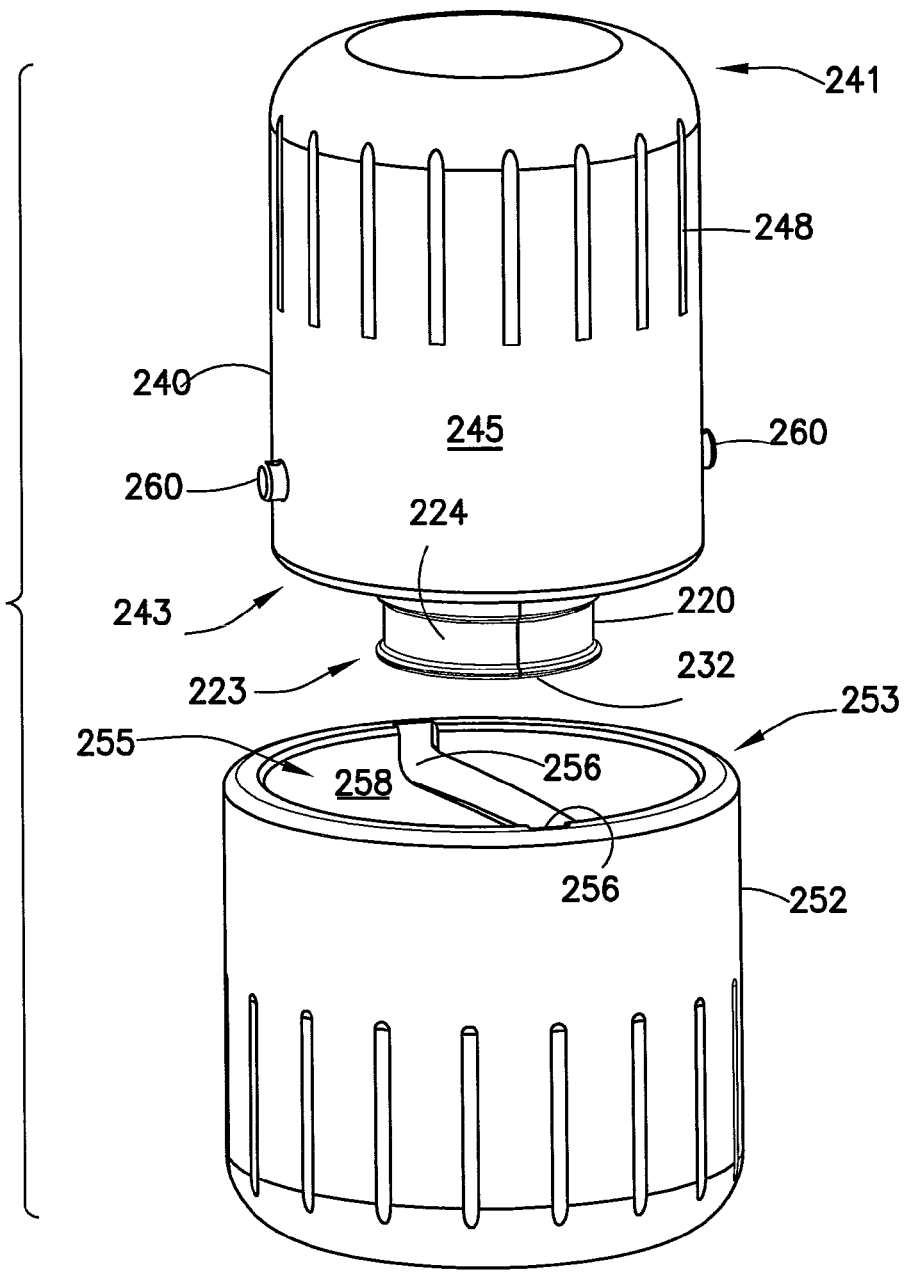

MOLECULAR IMAGING VIAL TRANSPORT CONTAINER AND FLUID INJECTION SYSTEM INTERFACE

CROSS REFERENCE TO RELATED APPLICATION

This application claims the benefit of U.S. Provisional Application No. 61/656,618, filed Jun. 7, 2012 entitled Molecular Imaging Vial Transport Container and Fluid Injection System Interface.

BACKGROUND OF THE INVENTION

1. Field of the Invention

This disclosure relates to generation, transportation, preparation, and administration of pharmaceutical substances, such as intrinsically harmful or toxic pharmaceutical substances such as radioactive pharmaceutical substances, generally known as radiopharmaceuticals to human and animal subjects and, further, to the administration of fluid pharmaceutical, typically radiopharmaceutical, substances to human and animal subjects.

2. Description of Related Art

As used herein, the term "pharmaceutical" refers to any substance to be injected or otherwise delivered into the body (either human or animal) in a medical procedure and includes, but is not limited, substances used in imaging procedures (for example, contrast media) and therapeutic substances. A number of such pharmaceutical substances pose a danger to both the patient and the personnel administering the substance if not handled and/or injected properly. Examples of hazardous pharmaceuticals include, but are not limited to, radiopharmaceuticals, biological pharmaceuticals, chemotherapeutic pharmaceuticals and gene therapeutic pharmaceuticals.

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue. Additionally, such radiopharmaceuticals may be used as therapeutic agents to kill or inhibit the growth of targeted cells or tissue, such as cancer cells. However, radiopharmaceutical agents used in imaging procedures and therapeutic procedures typically include highly radioactive nuclides of short half-lives and are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. However, due to the short half-life of typical radiopharmaceutical agents and small applied dosages, the radiation exposure risk to benefit ratio for individual patients is acceptable. The constant and repeated exposure of medical personnel and patients to radiopharmaceuticals over an extended period of time is a significant problem in the nuclear medicine field.

A number of techniques are used in the medical field to reduce radiation exposure to attending medical personnel associated with the creation, handling, transport, dose preparation, and administration of radiopharmaceuticals to patients. These techniques encompass one or more of minimizing the time of exposure of medical personnel, maintaining distance between medical personnel and the source of radiation, and/or shielding medical personnel from the source of radiation. As a certain amount of close-proximity interfacing between medical personnel and radiopharmaceutical agents (including patients who have or are to receive radiopharmaceutical agents) is somewhat inevitable during the current practice of generating, preparing, and administering radiopharmaceutical agents to patients and caring for these patients, radiation shielding has considerable importance in the nuclear medicine field. A simple patient radiation guard is disclosed in U.S. Pat. No. 3,984,695 to Collica et al. as an example. It is well-known, for example, to use shielded containers known as "pigs" or "pots" for general handling and transport of radiopharmaceutical containers (bottles, vials, etc.) and use shielded syringes to remove the radiopharmaceutical from the radiopharmaceutical containers and administer the same to individual patients. Radiopharmaceutical transport pigs are also configured to transport syringes. Examples of shielded transport pigs are disclosed in U.S. Pat. No. 5,274,239 to Lane et al. and U.S. Pat. No. 6,425,174 to Reich. Examples of shielded syringes are disclosed in U.S. Pat. No. 4,092,546 to Larrabee and U.S. Pat. No. 4,307,713 to Galkin et al. Other shielded syringes are known from U.S. Pat. No. 6,589,158 to Winkler; U.S. Patent Application Publication No. 2004/0015038 to Lemer; and U.S. Pat. No. 6,162,198 to Coffey et al.

As is generally known in the nuclear medicine field, radiation emanates in all directions from radioactive substances and, consequently, emanates in all directions from an unshielded container holding a radioactive substance. While radiation may be scattered or deflected, this effect is generally small enough that it is sufficient to protect personnel from the direct "shine" of radiation, unless the activity levels in the container are very high. Transport pigs come in various configurations for holding radiopharmaceutical containers (bottles, vials, syringes, etc.). One form often includes a removable cover that allows access to the held radiopharmaceutical container, as disclosed in U.S. Patent Application Publication No. 2005/0107698 to Powers et al. Such containers may be in the form of a vial with an elastomeric, for example rubber, stopper or septum which retains the radiopharmaceutical agent in the vial. When the pig cover is in place, the radiation exposure is acceptable. When the cover is opened or removed, a radiation "shine" emanates from the opening. A common sterile transfer procedure to remove the radiopharmaceutical agent from its container is to pierce the elastomeric stopper or septum with a sterile needle on a syringe. Commonly, the exposed surface of the stopper or septum is sterilized with an alcohol wipe prior to piercing the stopper or septum with the transfer needle on the syringe.

Syringes, during loading and once loaded with radiopharmaceutical agents, are commonly handled via syringe shields and shielded glove boxes or containers, but may also be transported in a suitably configured transport pig as noted previously. Syringe shields are commonly hollow cylindrical structures that accommodate the cylindrical body of the syringe and are constructed of lead or tungsten with a lead glass window that allows the handler to view the syringe plunger and liquid volume within the syringe. Due to its cylindrical configuration, syringe shields protect against radiation emissions in a generally radial direction along the length of the syringe body, but the two open ends of the syringe shield provide no protection to the handler as there is radiation "shine" emanating from the two ends of the syringe shield. Devices are further known for drawing radiopharmaceutical agents into syringes. For example, U.S. Pat. No. 5,927,351 to Zhu et al. discloses a drawing station for handling radiopharmaceuticals for use in syringes. In radiopharmaceutical delivery applications, devices are known for remotely administering radioactive substances from syringes to minimize radiation exposures to attending medical personnel as disclosed in U.S. Pat. No. 5,514,071 to Sielaff, Jr. et al. or U.S. Pat. No. 3,718,138 to Alexandrov et al. An automated device for controlled administering radioactive substances is disclosed in U.S. Pat. No. 5,472,403 to Comacchia et al. A system approach to controlling injectors used to inject radioactive material into a patient is disclosed in published German Document No. DE 10 2005 010152.

In addition to the difficulties introduced by the hazardous nature of radiopharmaceuticals, the short half-lives of such radiopharmaceuticals further complicate the administration of a proper dosage to a patient. The radioactivity levels of the radiopharmaceutical agents used as tracers in, for instance, single-photon emission computerized tomography (SPECT), and positron emission tomography (PET), imaging procedures are measured by medical personnel, such as radiopharmacists or nuclear medicine technologists, to determine the radiation dose that will be administered to the individual during the course of a diagnostic procedure. The radiation dose received depends on a number of factors including the half-life of the radiopharmaceutical agent and the initial radioactivity level of the radiopharmaceutical agent at the time it is injected into the individual. One known solution is to measure or calibrate the initial radioactivity of the radiopharmaceutical and time the injection so that a dose of the desired level of radioactivity is delivered (as calculated from the half-life of the radiopharmaceutical). Often, radiation levels are determined as part of the dispensing or container-filling process as disclosed generally in U.S. Patent Application Publication No. 2006/0151048 to Tochon-Danguy et al., or measured by a stand-alone device adapted to receive the radiopharmaceutical container as disclosed in U.S. Pat. No. 7,151,267 to Lemer or U.S. Pat. No. 7,105,846 to Eguchi. Radiation detectors have also been placed upon syringe shields and in-line with the radiopharmaceutical delivery system. For example, U.S. Pat. No. 4,401,108 to Galkin et al. discloses a syringe shield for use during drawing, calibration, and injection of radiopharmaceuticals. This syringe shield includes a radiation detector for detecting and calibrating the radioactive dosage of the radiopharmaceutical drawn into the syringe. A similar arrangement to that disclosed by Galkin et al., but in connection with a transport pig, is disclosed in Japanese Publication No. JP 2005-283431 assigned to Sumitomo Heavy Industries. U.S. Pat. Nos. 4,562,829 and 4,585,009 to Bergner and Barker et al., respectively, disclose strontium-rubidium infusion systems and a dosimetry system for use therein. The infusion system includes a generator of the strontium-rubidium radiopharmaceutical in fluid connection with a syringe used to supply pressurized saline. Saline pumped through the strontium-rubidium generator exits the generator either to the patient or to a waste collection container. Tubing in line between the generator and the patient passes in front of a dosimetry probe to count the number of disintegrations that occur. As the geometric efficiency (or calibration) of the detector, the flow rate through the tubing, and volume of the tubing are all known quantities, it is possible to measure the total activity delivered to the patient (for example, in milliCuries). Likewise, radiation measurements have been made upon blood flowing through the patient. For example, U.S. Pat. No. 4,409,966 to Lambrecht et al. discloses shunting of blood flow from a patient through a radiation detector. A significant quantity of information about nuclear medicine imaging devices and procedures can be found in WO 2006/051531 A2 and WO 2007/010534 A2 from Spectrum Dynamics LLC., incorporated herein by reference. A portable fluid delivery unit is further known from U.S. Pat. No. 6,773,673 to Layfield et al.

As noted above, examples of the use of radiopharmaceutical agents in diagnostic imaging procedures include positron emission tomography (PET), and single-photon emission computerized tomography (SPECT), which are noninvasive, three-dimensional imaging procedures that provide information regarding physiological and biochemical processes in patients. In effect, the radiopharmaceutical agent acts as a tracer to interact with the targeted area. An initial step in producing PET images or SPECT images of, for example, vasculature, organs and organ systems, and/or other targeted tissue, is to inject the patient with a dose of the radiopharmaceutical agent. The radiopharmaceutical agent is absorbed on or by certain cells in the body structure of interest and concentrates in this area. As an example, fluorodeoxyglucose (FDG) is a slight modification to the normal molecule of glucose, the basic energy fuel of cells, which readily accepts a radionuclide as a replacement to one of the atoms of the molecule. The radiopharmaceutical "tracer" emits a positron which creates photons that can be detected as the tissue is scanned at various angles and the photons pass through a detector array. A computer is used to reconstruct a three-dimensional color tracer image of the selected tissue structure.

With the foregoing background now presented, exemplary practice of generating, preparing, and administration of radiopharmaceuticals will now be described. Typical radiopharmaceutical treatment practice in the United States includes having the radiopharmaceutical agent initially generated off-site from a treatment location, typically a hospital, by an outside nuclear medicine facility and then delivered to the treatment location for further preparation, for example, individual dosing and administration. The treatment location, for example a hospital, orders specific radioactive substances to be ready at specific times for specific patients. These substances are prepared by the outside nuclear medicine facility and with sufficient radioactivity that they will have the desired radioactivity level at the targeted time. For example, the outside nuclear medicine provider may have a facility equipped with a cyclotron or radioisotope generator in, for example, a lead-shielded enclosure wherein the radiopharmaceutical agent, namely, a radioactive isotope is generated or created. Further refining or dose preparation steps, namely, placing the radioisotope in injectable form, may occur at the off-treatment site. Thus, the outside provider may provide a radiopharmaceutical substance to the treatment site having a desired radioactivity level at the targeted time. Further "individual" dose preparation of the radiopharmaceutical agent may occur at the treatment site. Alternatively, the outside provider may provide a "finished" radiopharmaceutical agent ready for injection to a specified patient at a specified time so that treatment site personnel are only required to confirm that the correct radioactive dosage is present in the radiopharmaceutical agent, for example, in a stand-alone radiation dosimetry device as described previously. During the forgoing process, there is frequent close-proximity contact with radioactive materials by personnel and, as described previously, handling and transport shielding devices are needed for the protection of these personnel.

Transport pigs are commonly employed to transport the radiopharmaceutical agents, which are individual doses prepared for individual patients, to the treatment facility. At the treatment facility, data about each unit dose is entered into a facility computer either manually or through reading a bar code, RFID tag, portable drive, or other similar data format, which may accompany or be on the transport pig or the radiopharmaceutical agent container. When it is time to deliver a specified unit dose to a specified patient, treatment facility personnel must remove, for example, a syringe or vial containing the radiopharmaceutical agent from the transport pig and confirm that the dose in the syringe or vial is within the range prescribed for that patient. Alternatively, the attending personnel must transfer the radiopharmaceutical agent to a shielded syringe as identified previously and confirm dosage. If the dose is too high, some is discarded into a shielded waste container. If the dose is too low, either a different syringe or vial is used and/or additional agent is loaded into the syringe or vial, if available. While it is possible for the attending treatment site personnel to be involved with dosage preparation, typical United States practice is to have the radiopharmaceutical agent delivered to the treatment site which will have the desired radioactivity level at the targeted time. Manual manipulation of the radiopharmaceutical agent at the treatment site is limited at the treatment site due to this procedure. Nonetheless, various manual checks are required to confirm that a correct radiopharmaceutical dose is ready for injection into a specific patient. These manual checks include visual inspections and radioactivity measurements as noted above.

As an example of the foregoing, in PET imaging, an injectable radiopharmaceutical agent such as, for instance, FDG (fluorodeoxyglucose) is fabricated in a cyclotron device at an outside nuclear medicine facility. Thereafter, the FDG is processed to be in a radiopharmaceutical form and is transferred in an individual dose container (i.e., vial, bottle, syringe, etc.), and the container loaded into a transport pig to prevent unnecessary radiation exposure to personnel, such as the radiopharmacist, technician, and driver responsible for creation, handling, and transport of the FDG from the cyclotron site to the PET imaging site. Since the half-life of FDG is short, approximately 110 minutes, it is necessary to quickly transport the FDG to the PET imaging site. Depending upon the elapsed transport time and the initial radioactivity level of the FDG at the time of fabrication, the radioactivity level of the FDG may need to be re-measured at the PET imaging site. As an example, if the radioactivity level is too high, the transport radio-pharmacist at the PET imaging site may be required to dilute the FDG with a diluent such as, for instance, saline solution, and remove part of the volume or extract fluid to reduce radioactivity prior to patient injection. During this entire process, the handling of FDG from creation-to-patient injection may be entirely manual. Within this process, shielding products, as described previously (i.e., transport pigs, syringe shields, L-blocks, etc.) are used to shield individuals from FDG. While shielding may reduce the radiation exposure of the radio-pharmacist, the radio-pharmacist may still be exposed to emissions from the radiopharmaceutical agent during the manual mixing, volume reduction, and/or dilution process needed to obtain the required dose. After injection, and often after an additional delay to allow the radiopharmaceutical to reach and be absorbed by the desired regions of interest in the body, the patient is typically placed on a moveable bed that slides by remote control into a circular opening of an imaging scanner referred to as the gantry. Positioned around the circular opening and inside the gantry are several rings of radiation detectors. In one type of radiation detector, each detector emits a brief pulse of light every time it is struck with a gamma ray coming from the radionuclide within the patient's body. The pulse of light is amplified by a photomultiplier converted to an electronic signal and the information is sent to the computer that controls the apparatus and records imaging data.

In the United States, it is also known to have radiopharmaceutical agents delivered in a multi-dose format to the treatment site. As a result, this multi-dose format must be divided into singular doses for individual patients at the treatment site. While it is possible that this division may occur at the point of injection or administration, it is more typical for a radio-pharmacist or nuclear medicine technologist to perform the dividing process in a "hot lab" at the treatment facility. Individual radiopharmaceutical doses are then transported to the administration location within the treatment facility where the doses are administered to specific patients.

In Europe, radiopharmaceutical creation and dose preparation practice differs from United States practice in that these actions typically all occur within a "hot lab" in the treatment facility, again typically, a hospital. As an example, the hospital itself typically has cyclotron or isotope generators (such as technetium generators manufactured by Mallinckrodt Inc., St. Louis, Mo.; Amersham Healthcare, 2636 South Clearbrook Drive, Arlington Heights, Ill. 60005; or GE Healthcare Limited, Amersham Place, Little Chalfont, Buckinghamshire, United Kingdom) in a shielded location in the "hot lab". Two manufacturers of shielded glove boxes are Comecer in Italy and Lemer Pax in France. Hospital personnel create or extract the radioactive isotope, perform additional chemistry steps necessary to formulate the radioactive drug (i.e., radiopharmaceutical) early in the day, and then prepare unit doses for individual patients, generally close to the time the patient is to be injected with the radiopharmaceutical. While an internal "hot lab" has advantages in minimizing hazardous material transport and improving internal information transfer, additional time and radiation burdens are placed on hospital staff as the measurement of radioactivity levels at the various steps still depends upon manual insertion of a container (i.e., a vial, bottle, or syringe) into a dose calibrator and then repeated adjustments of the radioactivity until the desired level is achieved. The unit dose radiation level is commonly recorded manually or by a printer.

Within the prior art, systems for delivering hazardous fluids are known as disclosed, for example, in U.S. Pat. No. 6,767,319 to Reilly et al. and U.S. Patent Application Publication Nos. 2004/0254525 to Uber, III et al. and 2011/0178359 to Hirschman et al., the disclosures of which are incorporated herein by reference. A commercial example of such systems for delivering hazardous fluids is the Intego™ PET Infusion System sold by Medrad, Inc. of Indianola, Pa.

Another system adapted to inject a radioactive liquid into a patient is disclosed in Japanese Publication No. JP 2000-350783 (see also U.S. Patent Application Publication No. 2005/0085682 to Sasaki et al.), assigned to Sumitomo Heavy Industries. This published patent application discloses a system which dispenses a volume of radioactive fluid into a coiled "medicine container" situated in a radiation measuring unit. When the prescribed radiation dose is accumulated in the coiled container, another syringe pushes saline through the coiled container and into a patient. A similar device and method is disclosed in Japanese Publication No. JP 2002-306609, also assigned to Sumitomo Heavy Industries.

PCT Application Publication No. WO 2004/004787, assigned to Universite Libre de Bruxelles—Hopital Erasme, discloses a method by which continuous measurement of radioactivity by dosimetry is eliminated. The disclosed method requires an initial calibration step, but thereafter radiation dose is calculated based on the predictable decay of radioactivity as a function of time. Japanese Publication No. JP 2004-290455, assigned to Nemoto Kyorindo KK, discloses a radiation-shielded injector system which withdraws FDG from prefilled syringes and allows other fluids such as saline to be administered. European Patent Application Publication No. EP 1616587, assigned to University of Zurich, discloses a radioactive fluid dispensing device that pushes FDG into tubing within a radiation dose calibrator prior to a saline injection that administers the FDG to the patient. U.S. Patent Application Publication Nos. 2005/0203329 and 2005/0203330 to Muto et al. disclose a robotic, automated system for extracting radioactive fluids from a vial or bulk container into a number of unit dose syringes. This system may have application in a hospital pharmacy setting. U.S. Patent Application Publication No. 2005/0277833, assigned to E-Z-EM, Inc., discloses an injection system for handling, mixing, dispensing, and/or injecting mixtures of pharmaceutical agents. Radiation dose is monitored by discrete detectors at several locations in the apparatus.

SUMMARY OF THE INVENTION

A continuing need exists for systems, devices, and methods capable of the generation, safe transportation, preparation, and administration of pharmaceutical substances and, typically, harmful or toxic pharmaceutical substances such as radioactive pharmaceutical substances or drugs, to human and animal subjects.

One embodiment described in detail herein comprises a pharmaceutical transport container, comprising a first body portion adapted to receive at least a portion of a pharmaceutical vial, a second body portion removably engaged with the first body portion to fully enclose the vial, and a ratcheting mechanism. The first body portion comprises a closed end defining an opening for establishing fluid connection with the vial. The second body portion has a distal end removably engaged with the first body portion and a proximal end. The ratcheting mechanism is connected to the proximal end of the second body portion and comprises a cap member rotationally connected to the proximal end of the second body portion, and at least one pawl element extending from one of the second body portion and an interior surface of the cap member and engaging at least one ratchet detent defined in the other of the second body portion and the interior surface of the cap member to permit rotation of the cap member relative to the second body portion upon application of rotational force of a predetermined amount.

The at least one pawl element may be spring-biased to engage the at least one ratchet detent in the interior surface of the cap member. The at least one pawl element may comprise a plurality of spring-biased pawl elements to engage a plurality of ratchet detents in the interior surface of the cap member. The second body portion may be removably connected to the first body portion by a bayonet connection between the first body portion and the second body portion. The first body portion may define a hollow interior cavity to accept at least a cap end of the vial and a vial spike adapter connected to the cap end. An end portion at the proximal end of the second body portion may be seated within an interior pocket defined in the cap member, and the at least one pawl element may be disposed in a transverse bore in the end portion and spring-biased into engagement with the at least one ratchet detent. The at least one pawl element may comprise a pair of opposed pawl elements disposed in respective transverse bores in the end portion, and the opposed pawl elements may be spring-biased into engagement with respective ones of a plurality of ratchet detents. The at least one pawl element may be spherical and spring-biased to engage the at least one ratchet detent in the interior surface of the cap member. The first body portion and the second body portion may be formed of radiation-shielding material. In use, upon application of the rotational force of the predetermined amount, the at least one pawl element disengages from the at least one ratchet detent, permitting rotation of the cap member relative to the second body portion. The first body portion may be formed as a clamshell movable from an open position to a closed position. The first body portion may comprise a first half hingedly connected to a second half to form the clamshell. A removable end cap may be used to cover the first body portion. The end cap may comprise an open proximal end, a closed distal end, and a receiving chamber to receive the first body portion therein to cover the opening in the closed end of the first body portion.

Another embodiment is directed to a pharmaceutical fluid injection system, which comprises a pharmaceutical transport container, a docking station, and a fluid connector mechanism axially disposed within the docking station. The pharmaceutical transport container comprises a first body portion adapted to receive at least a portion of a pharmaceutical vial, a second body portion removably engaged with the first body portion to fully enclose the vial, and a ratcheting mechanism. The first body portion comprises a closed end defining an opening for establishing fluid connection with the vial. The second body portion has a distal end removably engaged with the first body portion and a proximal end. The ratcheting mechanism is connected to the proximal end of the second body portion and comprises a cap member rotationally connected to the proximal end of the second body portion, and at least one pawl element extending from one of the second body portion and an interior surface of the cap member and engaging at least one ratchet detent defined in the other of the second body portion and the interior surface of the cap member to permit rotation of the cap member relative to the second body portion upon application of rotational force of a predetermined amount. The docking station may be provided on the pharmaceutical fluid injection system and comprises a guide collar to receive the pharmaceutical transport container therein. The fluid connector mechanism is axially disposed within the docking station and comprises a fluid connector element to establish fluid connection with the vial in the pharmaceutical transport container. The fluid connector element may be supported by a spring-biased collar. The guide collar may have a plurality of spring arms to engage an exterior surface of the second body portion.

The at least one pawl element may be spring-biased to engage the at least one ratchet detent in the interior surface of the cap member. The at least one pawl element may comprise a plurality of spring-biased pawl elements to engage a plurality of ratchet detents in the interior surface of the cap member. The second body portion may be removably connected to the first body portion by a bayonet connection between the first body portion and the second body portion. The first body portion may define a hollow interior cavity to accept at least a cap end of the vial and a vial spike adapter connected to the cap end. An end portion at the proximal end of the second body portion may be seated within an interior pocket defined in the cap member, and the at least one pawl element may be disposed in a transverse bore in the end portion and spring-biased into engagement with the at least one ratchet detent. The at least one pawl element may comprise a pair of opposed pawl elements disposed in respective transverse bores in the end portion, and the opposed pawl elements may be spring-biased into engagement with respective ones of a plurality of ratchet detents. The at least one pawl element may be spherical and spring-biased to engage the at least one ratchet detent in the interior surface of the cap member. The first body portion and the second body portion may be formed of radiation-shielding material. In use, upon application of the rotational force of the predetermined amount, the at least one pawl element disengages from the at least one ratchet detent, permitting rotation of the cap member relative to the second body portion. The first body portion may be formed as a clamshell movable from an open position to a closed position. The first body portion may comprise a first half hingedly connected to a second half to form the clamshell. A removable end cap may be used to cover the first body portion. The end cap may comprise an open proximal end, a closed distal end, and a receiving chamber to receive the first body portion therein to cover the opening in the closed end of the first body portion.

In another aspect, a method of loading a pharmaceutical vial container in a pharmaceutical transport container is disclosed. The method includes a step of providing the pharmaceutical transport container, which comprises a first body portion defining a hollow interior cavity adapted to receive at least a portion of the vial therein, and comprising a closed distal end defining an opening, a second body portion removably engageable with the first body portion, the second body portion having a distal end removably engageable with the first body portion and a proximal end, and a ratcheting mechanism connected to the proximal end of the second body portion. The ratcheting mechanism comprises a cap member rotationally connected to the proximal end of the second body portion and at least one pawl element extending from one of the second body portion and an interior surface of the cap member and engaging at least one ratchet detent defined in the other of the second body portion and the interior surface of the cap member to permit rotation of the cap member relative to the second body portion upon application of rotational force of a predetermined amount.

The method further comprises a step of loading the vial into the hollow interior cavity of the first body portion, the vial comprising a vial spike adapter having a connecting tip extending through the opening in the closed distal end of the first body portion. Additionally, the method includes a step of connecting the second body portion to the first body portion to fully enclose the vial in the assembled transport container.

The first body portion may be formed as a clamshell comprising a first half hingedly connected to a second half. The first half and the second half may be movable from an open position to a closed position, and the step of loading the vial into the hollow interior cavity of the first body portion may further comprise moving the two halves to the closed position to secure the vial in the hollow interior cavity.

Moreover, the step of connecting the second body portion to the first body portion may comprise connecting the distal end of the second body portion with a proximal end of the first body portion.

Another embodiment of a pharmaceutical transport container described herein comprises a first body portion adapted to receive at least a portion of a pharmaceutical vial and a second body portion engaged with the first body portion to fully enclose the vial. The first body portion defines an opening for establishing fluid connection with the vial and comprises a proximal end. The second body portion has a distal end engaged with the proximal end of the first body portion and a closed proximal end and defining an interior cavity therebetween. The second body portion is adapted to cooperate with a receiving docking station of a fluid injection system to establish a fluid connection between the vial and a fluid connector element disposed within the docking station as the second body portion is inserted axially into the docking station. A guide tab may extend radially from an exterior surface of the second body portion or within the docking station, wherein the at least one guide tab is configured to engage at least one guide slot defined in the exterior surface of the second body portion or defined within the receiving docking station, such that engagement of the at least on guide tab with the at least one guide slot causes the second body portion to translate axially into the docking station to establish the fluid connection between the vial and the fluid connector element disposed within the docking station as a result of the axial translation. The guide slot may be helical.

A flexible ring configured to engage the first body portion may be positioned in an interior cavity of the second body portion, wherein the first body portion is configured to cause radial deformation of the flexible ring upon engagement of the first body portion and the second body portion. The first body portion comprises a radially-outward extending rim cooperating with the flexible ring to cause radial deformation of the flexible ring. The flexible ring may be elliptically-shaped, and the radially-outward extending rim may have an outer diameter greater than an inside distance across a minor axis of the flexible ring. Further, the first body portion could define a proximally extending wall configured to receive and surround the vial body and being receivable within the second body portion interior cavity.

Yet another embodiment of a pharmaceutical transport container may comprise a first body portion adapted to receive at least a portion of a pharmaceutical vial, a second body portion engaged with the first body portion to fully enclose the vial, and a removable end cap. The first body portion defines an opening for establishing fluid connection with the vial and comprises a proximal end. The second body portion has a distal end engaged with the proximal end of the first body portion and a closed proximal end and defining an interior cavity therebetween. The removable end cap comprises an open proximal end, a closed distal end, and a receiving chamber to receive the first body portion therein to cover the opening. The second body portion may be adapted to cooperate with the receiving chamber of the end cap such that the second body portion is guided axially into the receiving chamber of the end cap. The container may include at least one guide tab extending radially from an exterior surface of the second body portion or within the receiving chamber of the end cap, the at least one guide tab engageable within a at least one guide slot defined in the exterior surface of the second body portion or within the receiving chamber, wherein the at least one guide slot is oriented such that engagement of the at least on guide tab with the at least one guide slot causes the second body portion to translate axially into the receiving chamber of the end cap. The guide slot may be helical. The first body portion may define a hollow interior cavity to accept at least a cap end of the vial and/or a radially-inward extending rim in the hollow interior cavity to engage a neck of the vial. Further, the first body portion may be formed as a clamshell movable from an open position to a closed position. The second body portion may comprise a retaining ring positioned in the interior cavity of the second body portion maintaining a flexible ring in the interior cavity and abutting a radially-outward extending rim defined on an exterior surface of the first body portion. The pharmaceutical transport, including the first body portion and the second body portion, may be formed of radiation-shielding material.

Another embodiment of a pharmaceutical fluid injection system may comprise a pharmaceutical transport container, a docking station, and fluid connector mechanism disposed within the docking station. The pharmaceutical transport container may comprise a first body portion adapted to receive at least a portion of a pharmaceutical vial and defining an opening for establishing fluid connection with the vial and comprising a proximal end and a second body portion engaged with the first body portion to fully enclose the vial. The second body portion may have a distal end engaged with the proximal end of the first body portion and a closed proximal end. The docking station axially receives the pharmaceutical transport container therein, and may comprise a fluid connector element to establish fluid connection with the vial as the pharmaceutical transport container is received axially into the docking station. The system may include at least one guide tab extending radially from an exterior surface of the second body portion or within the docking station, the at least one guide tab configured to engage at least one guide slot defined in the exterior surface of the second body portion or defined within the receiving docking station, the at least one guide slot oriented such that engagement of the at least on guide tab with the at least one guide slot causes the second body portion to translate axially into the docking station to establish the fluid connection between the vial and a fluid connector element disposed within the docking station as a result of the axial translation. The docking station could comprise a guide collar defining the guide slot on an interior surface thereof. The guide slot could be helical. The fluid connector element could comprise a vial spike to puncture a vial stopper at a cap end of the vial. A flexible ring may be positioned in an interior cavity of the second body portion and configured to engage the first body portion. The first body portion could include a radially-outward extending rim cooperating with the flexible ring, which may be elliptically-shaped. The radially-outward extending rim could be configured to cause radial deformation of the flexible ring when the first body portion is inserted into the second body portion. The radially-outward extending rim could include an outer diameter greater than an inside distance across the flexible ring. The first body portion could define a proximally extending wall configured to receive and surround the vial body and being receivable within the second body portion interior cavity.

A method of loading a pharmaceutical vial container in a pharmaceutical fluid may include the steps of providing a pharmaceutical transport container, providing a docking station, and loading the transport container in the docking station. The step of providing the pharmaceutical transport container could include a transport container including a first body portion defining a hollow interior cavity adapted to receive at least a portion of the vial therein, and defining an opening for establishing fluid connection with the vial and a proximal end; and a second body portion removably engageable with the first body portion, the second body portion having a distal end removably engageable with the proximal end of the first body portion and a closed proximal end. The second body portion may include at least one guide tab extending from an exterior surface of the second body portion.

The docking station may receive the pharmaceutical transport container therein, the docking station comprising a fluid connector element to establish fluid connection with the vial. Loading the transport container may include engaging the at least one guide tab in at least one guide slot, wherein the guide slot is oriented to cause the second body portion to translate axially into the docking station such that the fluid connector element and the vial are placed in fluid communication as a result of the axial translation.

The fluid connector element could comprise a vial spike, wherein the step of loading the transport container in the docking station causes automatic piercing of a stopper in a cap of the pharmaceutical vial. The guide tab could extend radially from an exterior surface of the second body portion or within the docking station, wherein the guide tab is configured to engage the at least one guide slot defined in the exterior surface of the second body portion or defined within the receiving docking station. The guide slot could be helically-shaped, wherein the transport container translates axially and rotationally in the docking station. The guide slot could define an end pocket, such that the method further includes the step of stopping the axial translation of the at least one guide tab in the guide slot as the at least one guide tab seats into the end pocket. The end pocket may be positioned to establish a preset axial distance between the fluid connector element and the vial sufficient to establish fluid communication between the fluid connector element and the vial. The fluid connector element could include a vial spike and the preset axial distance could be established to cause automatic piercing of a stopper in a cap of the pharmaceutical vial during the step of loading the transport container in the docking station. The preset axial distance may be selected to prevent over-insertion of the transport container into the docking station.

A further embodiment is directed to a method of loading a pharmaceutical vial in a pharmaceutical fluid injection system, that includes providing the pharmaceutical transport container summarized above, providing a docking station to receive the pharmaceutical transport container therein, the docking station comprising a fluid connector element to establish fluid connection with the vial, and loading the pharmaceutical transport container in the docking station by engaging at least one guide tab in at least one guide slot. The at least one guide slot may be oriented to cause the second body portion to translate axially into the docking station such that the fluid connector element and the vial are placed in fluid connection as a result of the axial translation.

The fluid connector element may comprise a vial spike and the step of loading the pharmaceutical transport container in the docking station may cause automatic piercing of a stopper in a cap of the pharmaceutical vial.

The at least one guide tab may extend radially from an exterior surface of the second body portion or within the docking station, and the at least one guide tab may be configured to engage the at least one guide slot defined in the exterior surface of the second body portion or defined within the receiving docking station. The at least one guide slot may be helically-shape, such that the pharmaceutical transport container translates axially and rotationally into the docking station.

The at least one guide slot may define an end pocket, the method may further comprise stopping axial translation of the at least one guide tab in the at least one guide slot as the at least one guide tab seats into the end pocket. The end pocket may be positioned to establish a preset axial distance between the fluid connector element and the vial sufficient to establish the fluid connection between the fluid connector element and the vial. The fluid connector element may comprise a vial spike and the preset axial distance may be established to cause automatic piercing of a stopper in a cap of the pharmaceutical vial during the step of loading the pharmaceutical transport container in the docking station. The preset axial distance may be selected to prevent over-insertion of the pharmaceutical transport container into the docking station.

Further details and advantages will become clear upon reading the followed detailed description with the accompanying drawing figures.

BRIEF DESCRIPTION OF THE DRAWINGS

FIG. 19 is a perspective view of another portion of the vial transport container of FIG. 17.

FIG. 20 is a perspective view of the vial transport container shown in FIG. 17, and further illustrating an end cap of the vial transport container.

FIG. 21 is an exploded view of the assembled vial transport container shown in FIG. 20.

DESCRIPTION OF THE PREFERRED EMBODIMENTS

Figure 1:
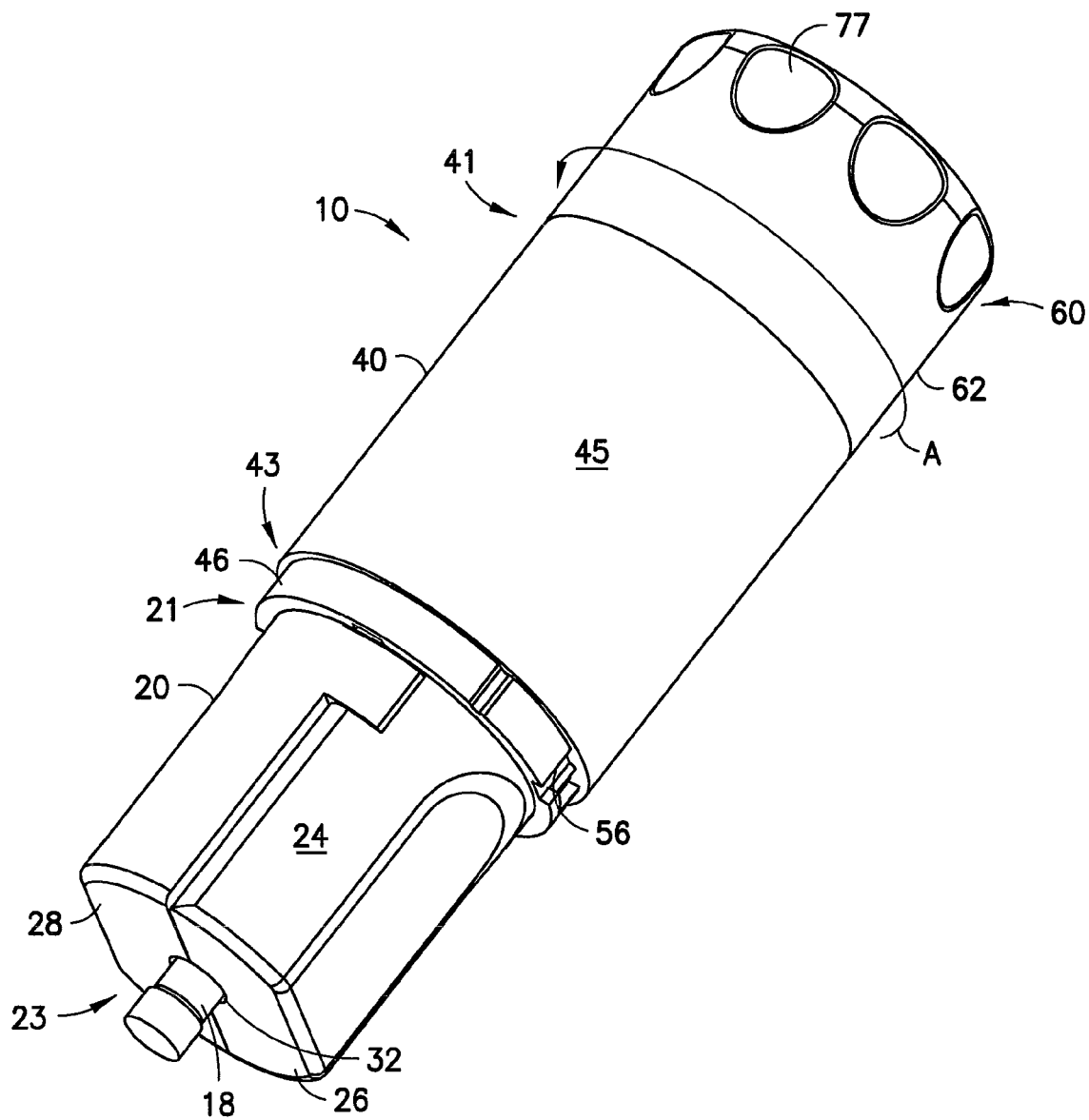
FIG. 1 is a perspective view of an embodiment of a vial transport container.

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Although the term "vial" is used herein throughout, and the embodiments described herein below describe use of a vial, it is contemplated that the below-described and claimed pharmaceutical transport container 10 and associated fluid injection mechanism or system 100 may encompass a variety of containers, including, but not limited to, bottles, syringes, and the like. Vials may be deemed an exemplary configuration for a container used to transport a medical fluid for injection into a patient.

Referring to FIGS. 1-8, a pharmaceutical transport container 10 for transporting a vial 12 may generally include a first or lower body portion 20, a second or upper body portion 40, and a ratcheting mechanism 60 operably associated with the second or upper body portion 40. The transport container 10, including the first body portion 20, the second body portion 40, and the ratcheting mechanism 60, may be constructed of radiation-shielding material. The radiation-shielding material may include machined tungsten, high specific gravity polymer, tungsten powder-nylon blends, and/or combinations thereof, and like radiation shielding materials. For example, the first body portion 20, the second body portion 40, and the ratcheting mechanism 60 may be constructed by injection molding a blend of tungsten powder and nylon.

The first body portion 20 includes an open proximal end 21 and a closed distal end 23 and defines a hollow interior cavity 22 therebetween. The first body portion 20 further has an exterior surface 24. The closed distal end 23 defines an opening 32 for a fluid connection element to extend through the closed distal end 23, such that the vial 12 disposed in the transport container 10 may be connected to a fluid injection mechanism or system 100, as described herein in connection with FIGS. 11-16, for delivery of a pharmaceutical or radiopharmaceutical to a patient. For example, the transport container 10, as described herein, may be used in conjunction with a molecular imaging infusion system and the fluid injection mechanism or system 100 described herein in connection with FIGS. 11-16, which may be an Intego™ PET Infusion System and like systems.

Figure 5:
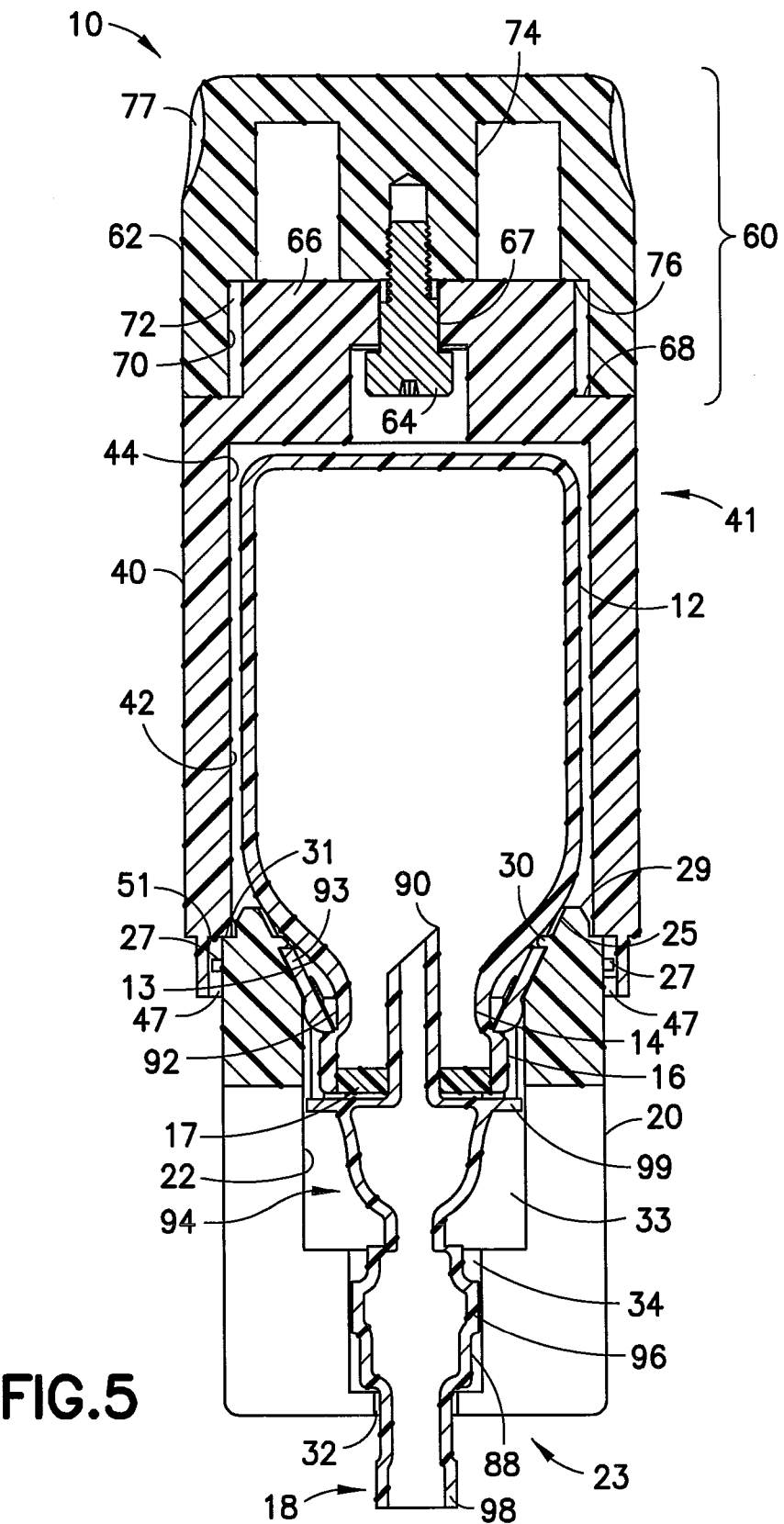
FIG. 5 is cross-sectional view taken along line 5-5 in FIG. 4.
Figure 7:
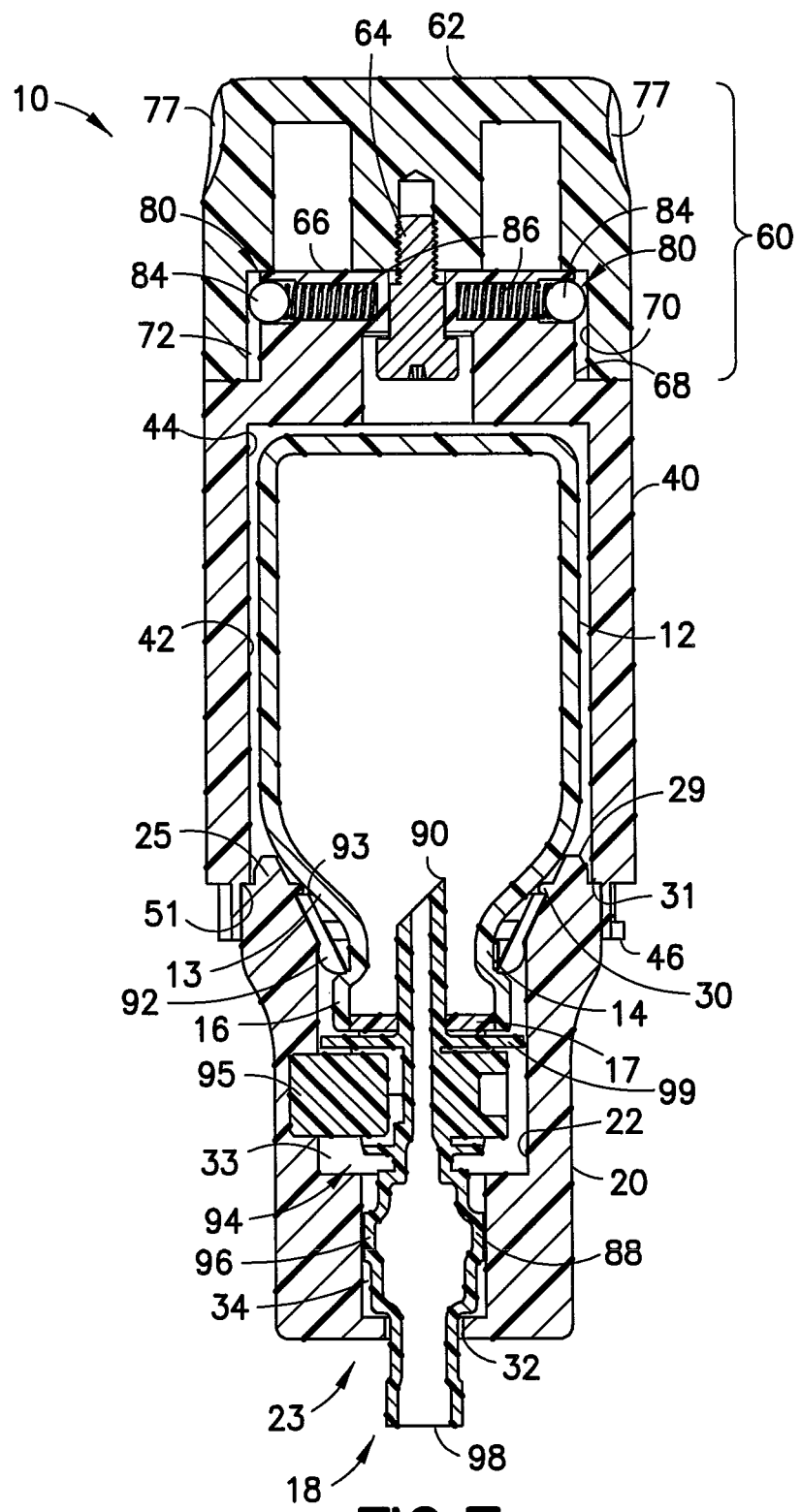
FIG. 7 is a cross-sectional view taken along line 7-7 in FIG. 4.

The second body portion 40 has a closed proximal end 41 and an open distal end 43. The second body portion 40 is typically hollow to define a hollow interior cavity 42, as best shown in FIGS. 5 and 7, having an interior surface 44. The second body portion 40 further comprises an exterior surface 45. Generally, the first body portion 20 and the second body portion 40 are configured to cooperatively receive, enclose, and support the vial 12. The vial 12 has a tapered end portion 13 that narrows to form a neck 14. The vial 12 has a cap end 16 sealed with a conventionally puncturable vial stopper 17. The neck 14 is defined intermediately between the tapered end portion 13 and the cap end 16, as shown in FIGS. 5 and 7. Referring specifically to FIGS. 5 and 7, the vial 12 may be filled with a pharmaceutical to be delivered to a patient or, in particular, a radiopharmaceutical for use in molecular imaging procedures. The interior of the vial 12 may be accessed using a vial spike adapter 18 inserted into and through the vial stopper 17. The vial spike adapter 18 permits fluid communication to be established between the interior of the vial 12 and, for example, the fluid injection mechanism or system 100, an embodiment of which is shown in FIGS. 11-16 discussed herein. Thus, the vial spike adapter 18 generally extends through the opening 32 in the closed distal end 23 of the first body portion 20 and provides a fluid connection element for establishing a fluid connection between the vial 12 and the fluid injection mechanism or system 100. The fluid path provided by the vial spike adapter 18 permits the fluid injection mechanism or system 100 to withdraw fluid from the interior of the vial 12 and deliver the pharmaceutical contents of the vial 12 to a patient. The vial 12 may optionally be an ISO compliant bulk vial and may range, for example, between 10 and 30 mL in volume, and the vial spike adapter 18 may be any suitable vial spike adapted to access the vial stopper 17 and provide a fluid connection point to the fluid injection mechanism or system 100.

The vial spike adapter 18 comprises a unitary vial spike body 88 having a spike 90 adapted to puncture the vial stopper 17 in the cap end 16 of the vial 12. The vial spike body 88 comprises an engagement portion 92 with a terminal edge or rim 93. The engagement portion 92 is adapted for a snap-fit connection onto the cap end 16 of the vial 12, whereby the engagement portion 92 snaps onto the cap end 16 and seats against the tapered end portion 13 of the vial 12. The vial spike body 88 further comprises a fluid conducting portion 94 that includes a side port access element or component 95 and a downstream, slightly enlarged, distal chamber 96, which leads to a connecting tip or end 98 of the vial spike adapter 18. The connecting tip or end 98 may be in the form of an internally or externally-threaded luer connector and typically extends or projects through the opening 32 in the closed distal end 23 of the first body portion 20 and provides a fluid connection element for establishing a fluid connection between the vial 12 and the fluid injection mechanism or system 100. An end flange 99 may be provided as part of the engagement portion 92 of the vial spike adapter 18 to seat against the cap end 16 of the vial 12 and stabilize the engagement between the vial spike adapter 18 and the cap end 16 of the vial 12.

The second body portion 40 is removably engageable with the first body portion 20. As shown, the open distal end 43 of the second body portion 40 may engage and mate with the open proximal end 21 of the first body portion 20, such that the open proximal end 21 of the first body portion 20 is received into the open distal end 43 of the second body portion 40. However, this specific configuration may be reversed if so desired. The open proximal end 21 of the first body portion 20 includes an interiorly tapered rim 25 that defines a proximally-extending lip or rim 29, a radially-inward extending lip or rim 30, and an exterior edge or rim 31. When the open proximal end 21 of the first body portion 20 is mated with the open distal end 43 of the second body portion 40, the proximally-extending lip or rim 29 is received into the open distal end 43 of the second body portion 40, with the exterior edge or rim 31 abutting a mating internal edge or rim 51 defined interiorly within the open distal end 43 of the second body portion 40. As shown, the first body portion 20 and the second body portion 40 may be secured in removable engagement by a bayonet connection therebetween. In this connection arrangement, the first body portion 20 includes at least one external protrusion 27 or, as shown a plurality of external protrusions 27, provided on the exterior surface 24 of the first body portion 20 and, in particular, on the exterior surface 24 of the first body portion 20 coextensive with the interiorly tapered rim 25. The open distal end 43 of the second body portion 40 includes a distal lip or rim 46 which defines an interior L-shaped bayonet slot 47 or, as shown, a plurality of such L-shaped bayonet slots 47 defined in the interior surface 44 of the second body portion 40 in the distal lip or rim 46. Other suitable and equivalent removable or detachable connecting arrangements may be substituted for the bayonet-type connection shown in the Figures, as this specific connection arrangement is exemplary and not intended to be limiting.

Figure 2:
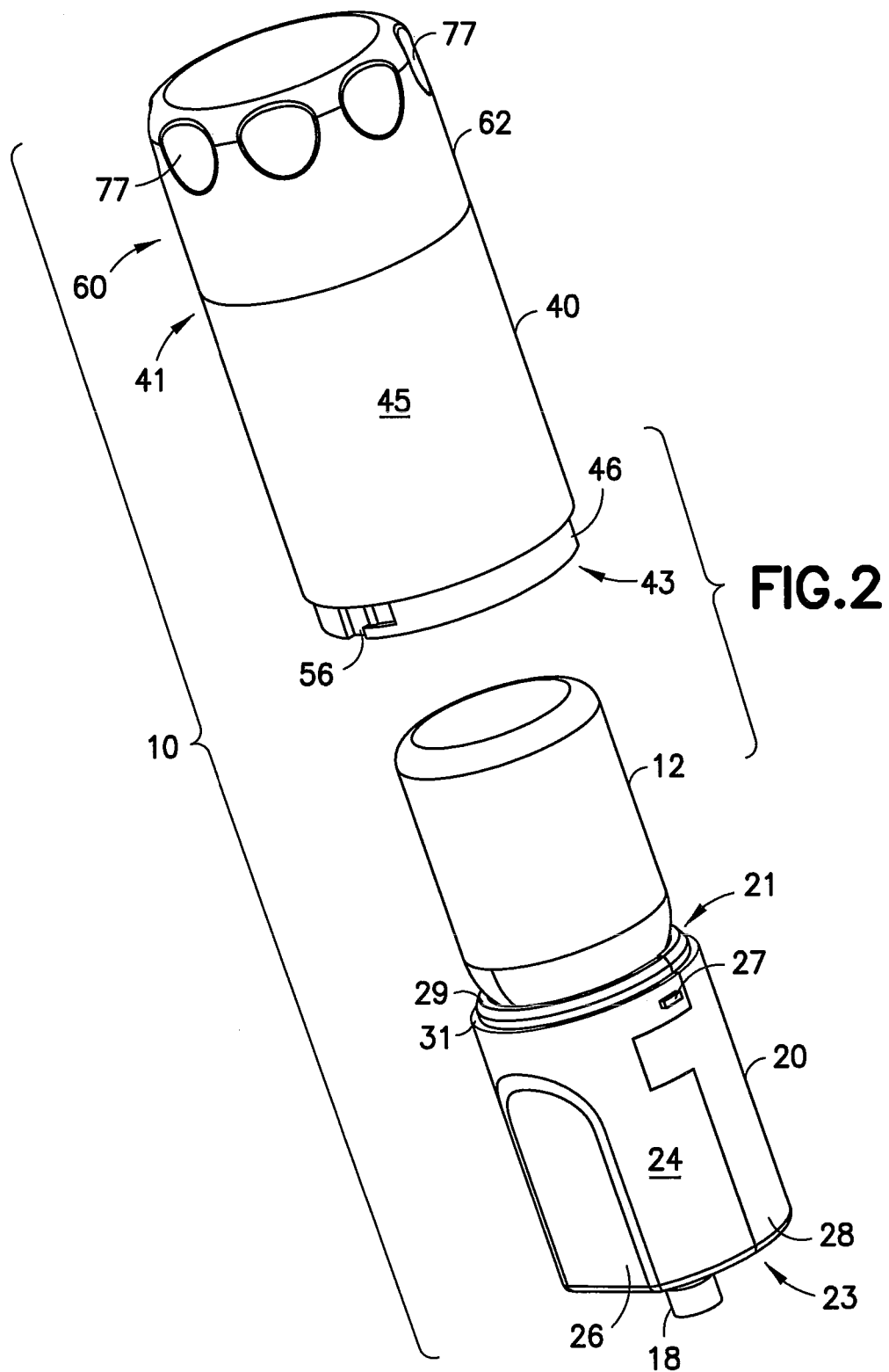
FIG. 2 is a partially exploded view of the vial transport container shown in FIG. 1.
Figure 3:
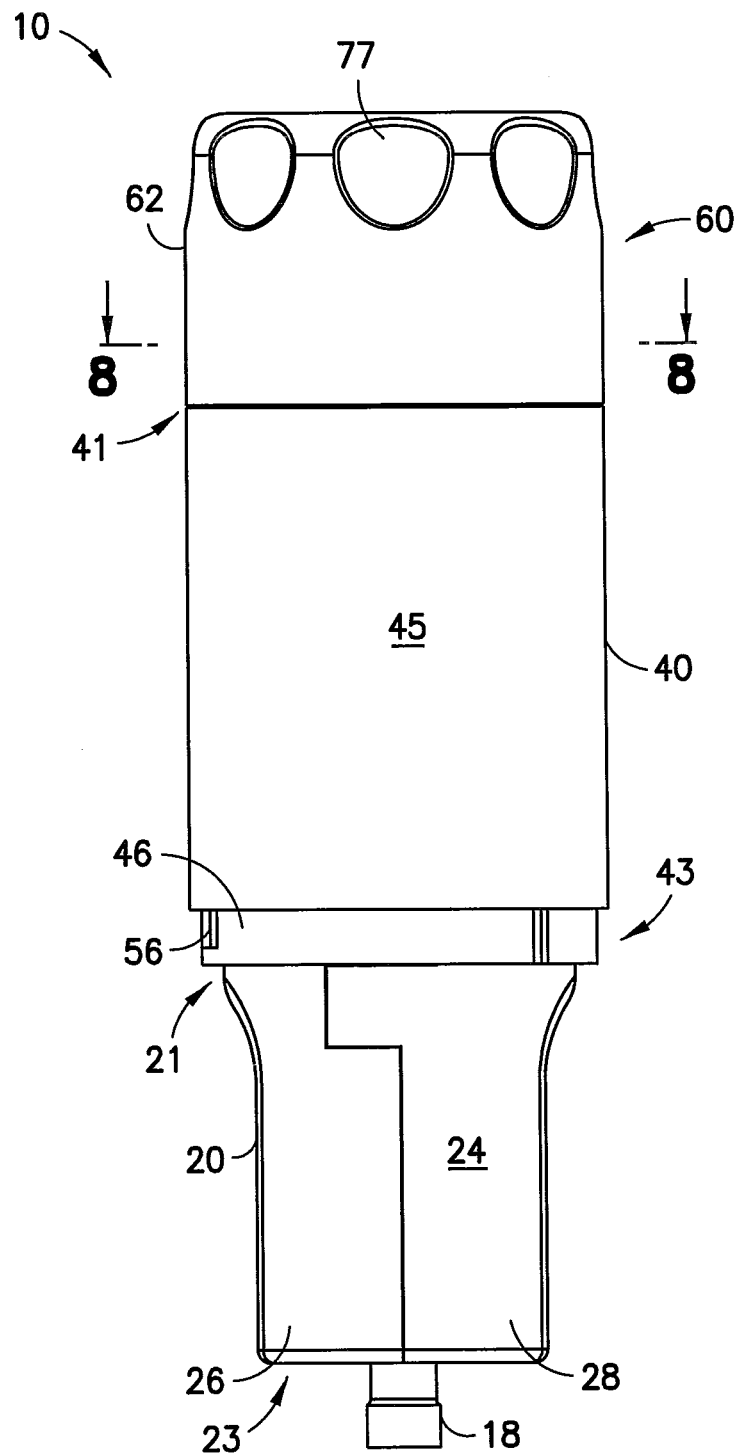
FIG. 3 is a side view of the vial transport container shown in FIG. 1.
Figure 4:
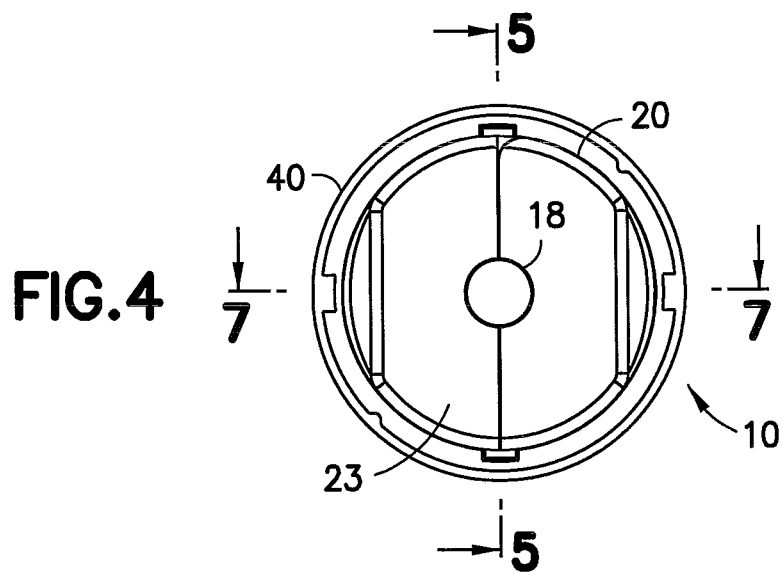
FIG. 4 is a bottom view of the vial transport container shown in FIG. 1.
Figure 6:
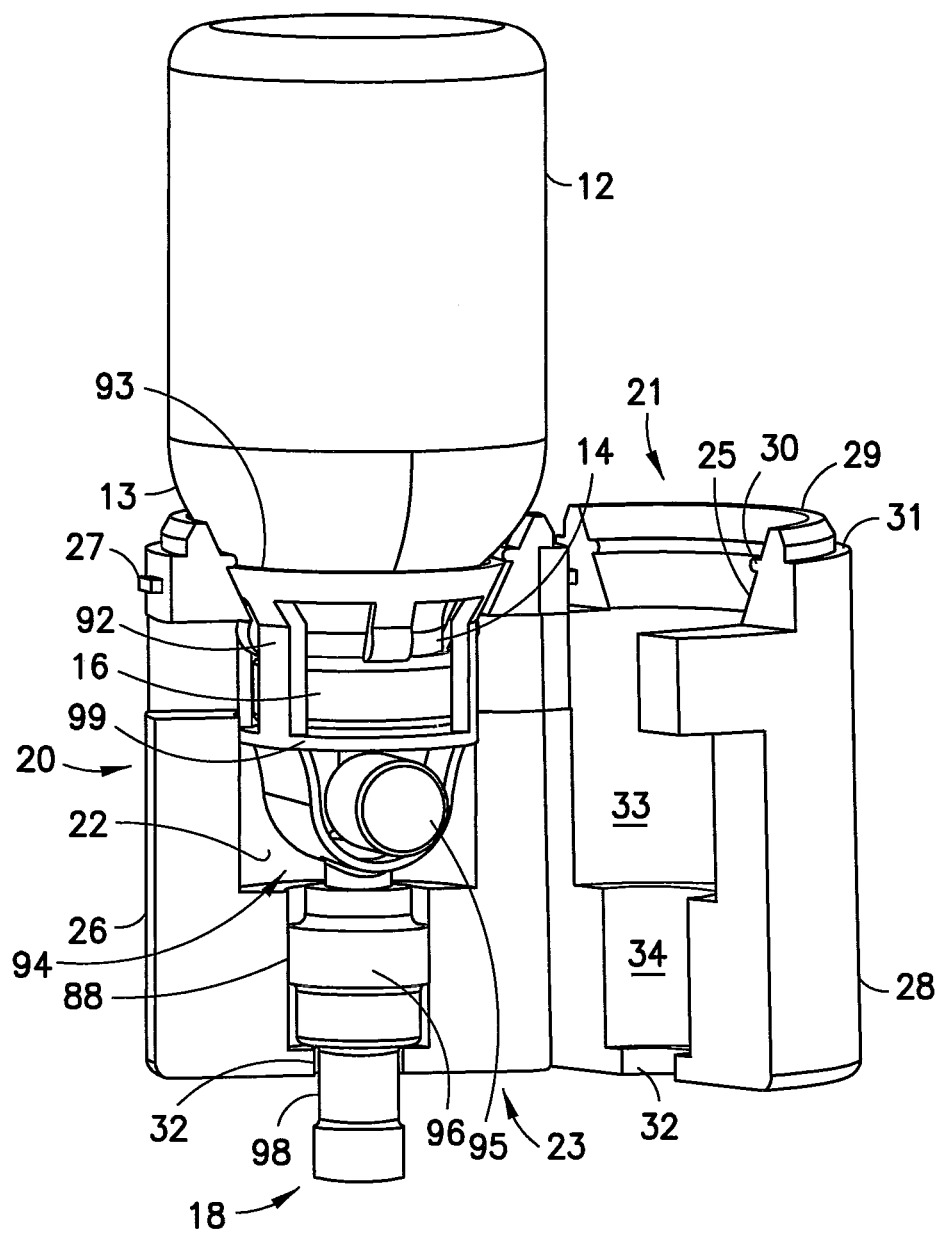
FIG. 6 is a perspective and partially exploded view of a portion of the vial transport container of FIG. 1 and showing a vial associated with the shown portion of the vial transport container.

As best shown in FIG. 6, the first body portion 20 may be constructed as a clamshell member. Thus, the clamshell first body portion 20 may be divided into a first half or portion 26 and a second half or portion 28, with the first half 26 and the second half 28 being hingedly connected with each other. In this manner, the first body portion 20 may be moved between a closed position as shown in FIG. 2, and an open position as shown in FIG. 6. In the open position, the vial 12 may be supported by one of the halves during the loading process, such as the first half or portion 26 as shown in FIG. 6. The second half or portion 28 may then be hingedly moved to abut the first half or portion 26 to enclose at least the discharge portion of the vial 12 (e.g., the tapered end portion 13, the neck 14, and the cap end 16 sealed with vial stopper 17). Additionally, the vial spike adapter 18 associated with the vial 12 may be enclosed and supported between the first half or portion 26 and the second half or portion 28 in the closed position of the first body portion 20.

The first body portion 20 defines an interior cavity 22 which accommodates the cap end 16 enclosed by the vial stopper 17, the tapered end portion 13 of the vial 12 and, further, the vial spike adapter 18. The interior cavity 22 comprises a larger bore top or proximal chamber 33 that is shaped to accommodate the side port access element 95 of the vial spike adapter 18, as well as the cap end 16 of the vial 12. The interior cavity 22 further comprises a smaller bore bottom or distal chamber 34 that is shaped to accommodate the distal chamber 96 leading to the connecting tip or end 98 of the vial spike adapter 18. As shown in FIGS. 5 and 7, when the vial 12 and attached vial spike adapter 18 are seated in the interior cavity 22 in the first body portion 20, the distal chamber 96 of the vial spike adapter 18 is disposed and supported within the bottom or distal chamber 34, with the connecting tip or end 98 of the vial spike adapter 18 extending through the opening 32 in the closed distal end 23 of the second body portion 20. Additionally, the engagement portion 92 of the vial spike adapter 18 is seated in the top or proximal chamber 33 and held in place therein by engagement of the radially-inward extending lip 30 on the interiorly tapered rim 25 on the first body portion 20. The radially-inward extending lip 30 engages the terminal end or rim 93 of the engagement portion 92 of the vial spike adapter 18 to maintain the positioning of the vial 12 in the interior cavity 22 of the first body portion 20. Moreover, the interiorly tapered rim 25 is desirably tapered to match the tapered shape of the engagement portion 92 of the vial spike adapter 18 so that there is generally uniform support around the circumference of the engagement portion 92 to enhance the support of the vial 12 and the attached vial spike adapter 18 in the first body portion 20. The interiorly tapered rim 25 further supports the tapered end portion 13 of the vial 12 as also shown in FIGS. 5 and 7. Thus, the top or proximal chamber 33 generally receives the cap end 16 sealed by the vial stopper 17 of the vial 12 and, further, the engagement portion 92 and the side port access element 95 of the vial spike adapter 18. The bottom or distal chamber 34 generally receives the distal chamber 96 and the connecting tip or end 98 of the vial spike adapter 18, with the connecting tip or end 98 extending through the opening 32 in the closed distal end 23 of first body portion 20. Lastly, the interiorly tapered rim 25 on the first body portion 20 is tapered to provide circumferential support to the engagement portion 92 of the vial spike adapter 18 and the tapered end portion 13 of the vial 12 to maintain the positioning of the vial 12 in the interior cavity 22 of the first body portion 20. The radially-inward extending lip 30 on the interiorly tapered rim 25 engages the terminal end or rim 93 of the engagement portion 92 of the vial spike adapter 18 to assist in maintaining the axial positioning of the vial 12 in the interior cavity 22 of the first body portion 20.

As noted previously, the first body portion 20 is removably engaged with the second body portion 40 via the mating engagement between the external protrusions 27 on the first body portion 20 with the L-shaped bayonet slots 47 defined in the interior surface 44 of second body portion 40 in the distal lip or rim 46. With this engagement, the proximally-extending lip or rim 29 on the interiorly tapered rim 25 at the open proximal end 21 of the first body portion 20 is received into the open distal end 43 of the second body portion 40, so that the exterior edge or rim 31 abuts the mating internal edge or rim 51 defined interiorly within the distal lip or rim 46 at the open distal end 43 of the second body portion 40. This overlapping engagement prevents radioactive "shine" from emitting outward from the transport container 10 at the interface between the first body portion 20 and the second body portion 40 should the vial 12 be filled with a radiopharmaceutical fluid.

Figure 8:
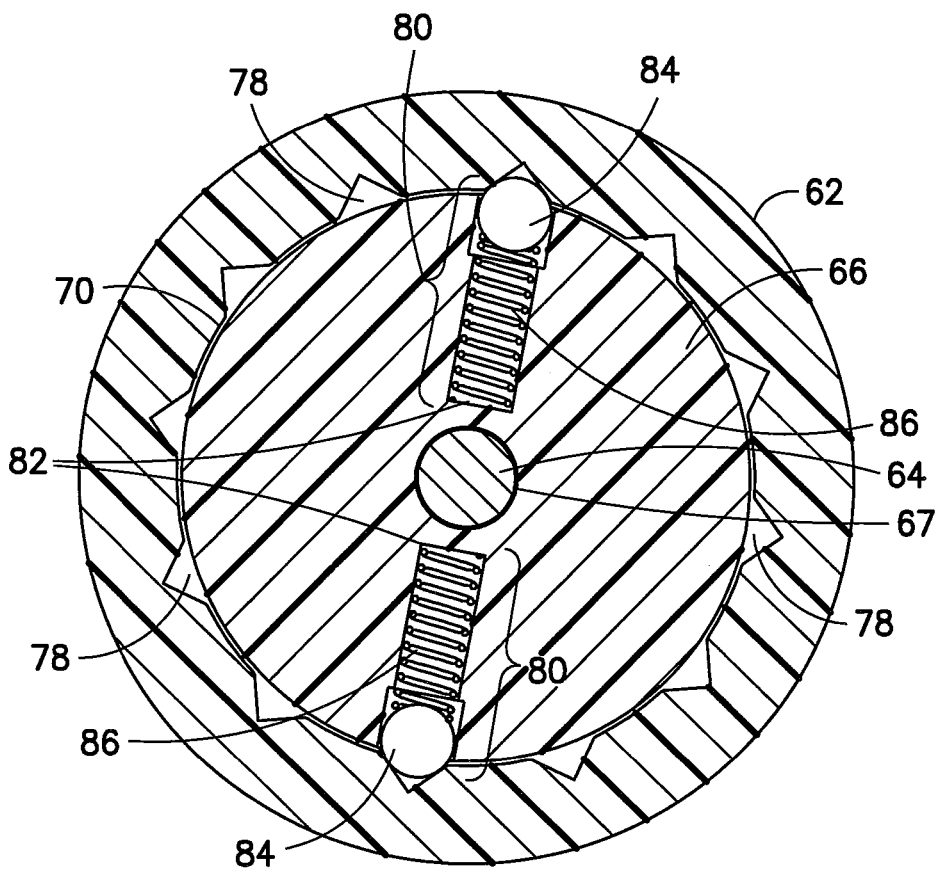
FIG. 8 is a cross-sectional view taken along line 8-8 in FIG. 3.

Additionally, as noted previously, the transport container 10 comprises a ratcheting mechanism 60 connected to the proximal end 41 of the second body portion 40, as best illustrated in FIGS. 5, 7, and 8. The ratcheting mechanism 60 includes a cap member 62 which is rotationally connected to the proximal end 41 of the second body portion 40 by a suitable rotational-permitting fastener 64. The proximal end 41 of the second body portion 40 comprises a narrowed end portion 66 that defines a central aperture 67 for the rotational fastener 64 and a circumferential ledge or edge 68 to rotationally support the cap member 62 thereon. The cap member 62 has an interior surface 70 and defines an interior cavity or pocket 72 for receiving the end portion 66 at the proximal end 41 of the second body portion 40. The cap member 62 also includes a central post portion 74 to which the rotational fastener 64 is joined to enable rotation of the cap member 62 relative to the second body portion 40. The central post portion 74 also contacts or engages the end portion 66 at the proximal end 41 of the second body portion 40. The interior surface 70 of the cap member 62 further defines an internal ledge 76 that contacts or engages the end portion 66 at the proximal end 41 of the second body portion 40. External detents 77 may be defined on the exterior of the cap member 62 for gripping by a user. The interior surface 70 of the cap member 62 further defines at least one and, desirably, a series of uniformly spaced ratchet detents 78, which may be notched or V-shaped as shown in FIG. 8. As illustrated, the end portion 66 at the proximal end 41 of the second body portion 40 is seated within the cap member 62, and the rotational fastener 64 secures the rotational connection between the cap member 62 and the proximal end 41 of the second body portion 40. The rotational fastener 64 also permits the cap member 62 and the proximal end 41 of the second body portion 40 to be removably engaged, such as by being threadably engaged, as illustrated.

As best shown in FIG. 8, the ratcheting mechanism 60 further includes a ratchet pawl 80 or, as depicted, a plurality of such pawls 80 associated with the end portion 66 at the proximal end 41 of the second body portion 40. In particular, a pair of opposite disposed ratchet pawls 80 is provided at the end portion 66 at the proximal end 41 of the second body portion 40. As noted previously, the interior surface 70 of the cap member 62 may define at least one and, as depicted, a plurality of ratchet detents 78. The opposed ratchet pawls 80 are adapted to engage the ratchet detents 78. This engagement permits rotation of the cap member 62 in at least one direction relative to the second body portion 40 upon application of a rotational force of a predetermined amount. Arrow A in FIG. 1 illustrates a direction of applied rotational force to the cap member 62 of the ratcheting mechanism 60, which is applied during installation of the transport container 10 to the fluid injection mechanism or system 100, as explained further herein.

As shown in FIG. 8, each ratchet pawl 80 is positioned in a transverse bore 82 defined in the end portion 66 at the proximal end 41 of the second body portion 40. Each ratchet pawl 80 comprises a pawl element 84 that is biased outward from the receiving bore 82 by a spring 86. As shown, the pawl elements 84 may be spherical. The force of the respective pawl springs 86 biases the pawl elements 84 into engagement with the ratchet detents 78 with a predetermined or preselected amount of force. As a result, a predetermined amount of rotational force is necessary to cause rotation of the cap member 62 on the second body portion 40, and this predetermined amount of rotational force is at least equal to the amount of force necessary to overcome the spring force biasing the pawl elements 84 into the ratchet detents 78. Once this predetermined amount of rotational force is applied, the pawl elements 84 disengage from the ratchet detents 78, thereby permitting rotation of the cap member 62 on the second body portion 40. This predetermined amount of rotational force can be preselected to prevent over-tightening of the fluid connection between the vial 12 and the transport container 10. In particular, this predetermined amount of rotational force can be preselected to prevent over-tightening of the fluid connection element on the vial spike adapter 18, namely the connecting tip or end thereof, and a mating fluid connection element associated with the fluid injection mechanism or system 100, explained in more detail herein.

Figure 9:
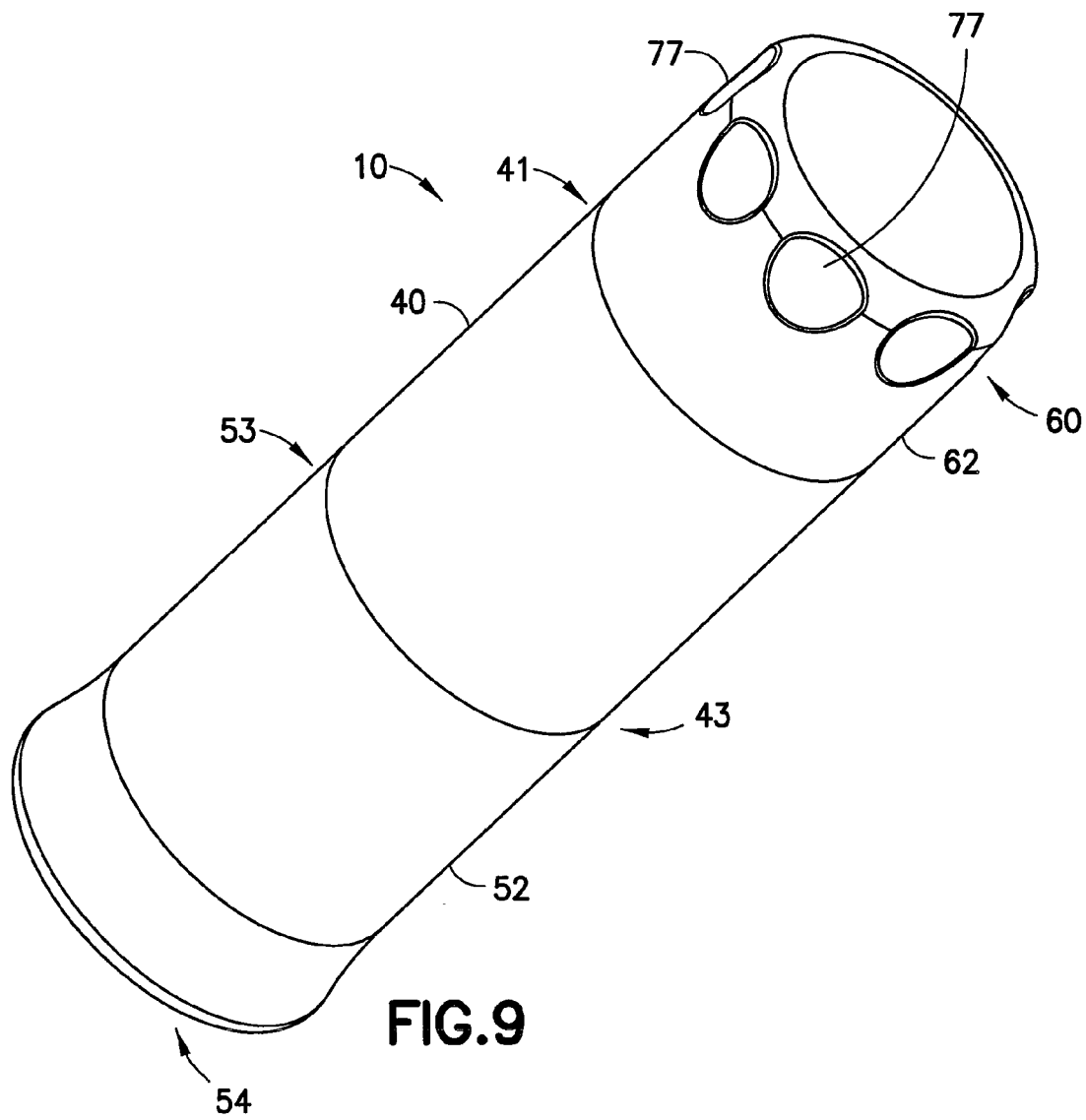
FIG. 9 is a perspective view of the vial transport container shown in FIG. 1, and further illustrating an end cap of the vial transport container.
Figure 10:
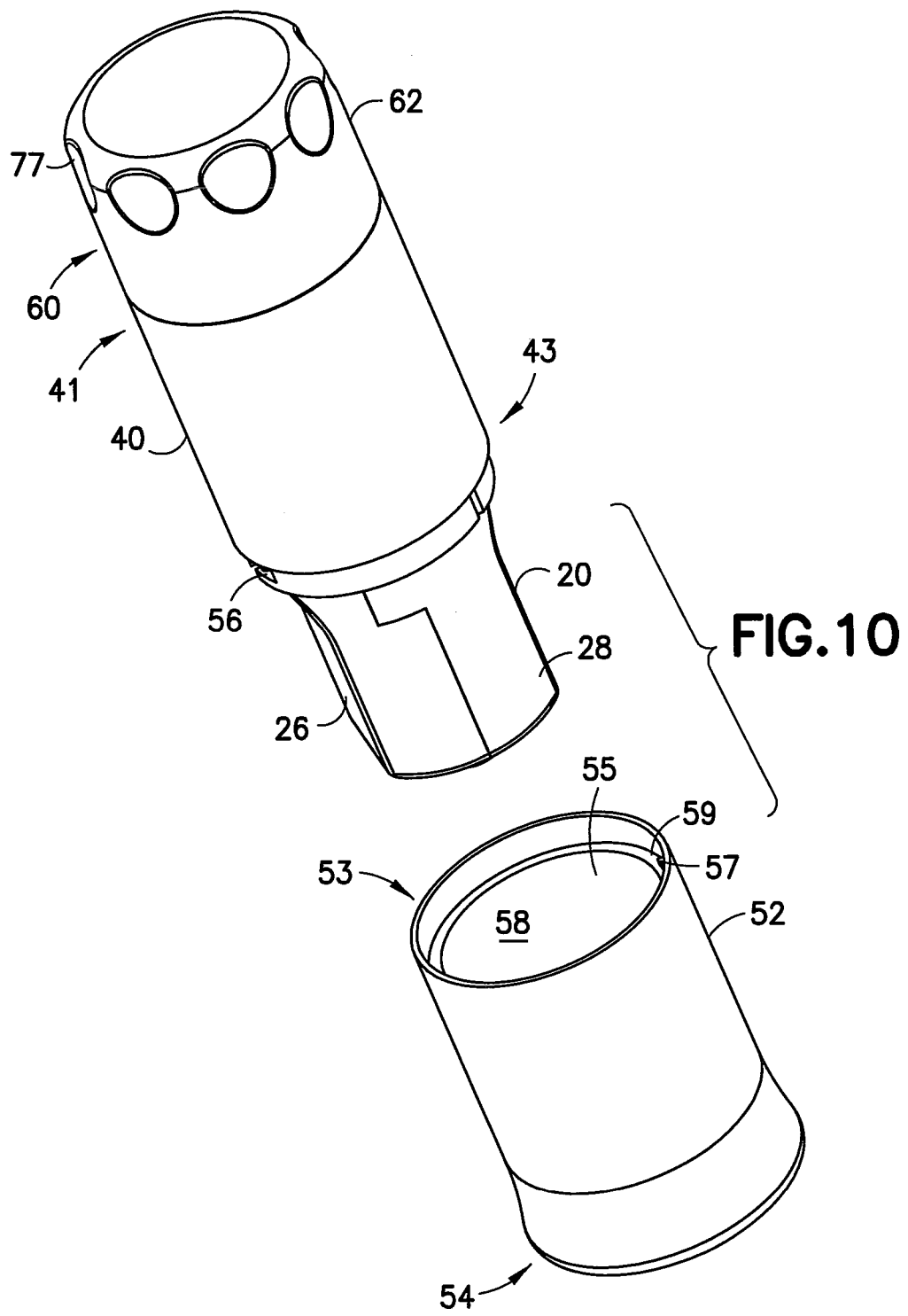
FIG. 10 is an exploded view of the vial transport container shown in FIG. 9.

Referring to FIGS. 9-10, another embodiment of the transport container 10 is shown and includes an optional end cap 52. The end cap 52 may be positioned over the first body portion 20, including the opening 32 with the connecting tip or end 98 of the vial spike adapter 18 extending therethrough. The end cap 52 includes an open proximal end 53 and a closed distal end 54 to define a receiving chamber 55 to receive at least the first body portion 20 therein. Because the vial spike adapter 18 is in fluid communication with the interior of the vial 12 and the vial 12 may be filled with a radiopharmaceutical, the opening 32 and the vial spike adapter 18 present a radiation exposure risk to a user, even though the first body portion 20 and the second body portion 40 both typically include radiation-shielding material. Therefore, the end cap 52 also typically includes radiation-shielding material, such as those materials discussed previously in connection with the first body portion 20 and the second body portion 40. The end cap 52 is generally positioned over the first body portion 20 during transportation of the transport container 10. The end cap 52 may be removably connected and engageable with the second body portion 40. For example, like the first body portion 20 connection to the second body portion 40, the end cap 52 may be removably connected to the second body portion 40 by a bayonet connection. In this connection, at least one exterior L-shaped slot 56 is provided on the distal lip or rim 46 provided at the open distal end 43 of the second body portion 40, and at least one mating protrusion 57 is provided interiorly on an interior surface 58 of the end cap 52. An abutment rim or flange 59 may be provided on the interior surface 58 of the mating protrusions 57, and which acts as a stop for engagement with the distal lip or rim 46 provided at the open distal end 43 of the second body portion 40.

Referring additionally to FIGS. 11-16, a pharmaceutical fluid injection mechanism or system 100 is generally shown.

In particular, FIGS. 11-16 illustrate an interface portion 110 of the fluid injection mechanism or system 100, which comprises a docking station 112 for the pharmaceutical transport container 10, described hereinabove. As explained previously, the first body portion 20 generally supports the vial 12 and the vial spike adapter 18. The fluid connection element for the transport container 10 is formed by the vial spike adapter 18, namely the connecting tip or end 98 thereof, which extends through the opening 32 in the closed distal end 23 of the first body portion 20. The docking station 112 is adapted to receive the transport container 10 so that the vial spike adapter 18 can be operably engaged with the fluid conducting components (not shown) of the fluid injection system 100, which could, for example, take the form of the Intego™ PET Infusion System sold by Medrad, Inc. of Indianola, Pa. As further described previously, the second body portion 40 cooperates with the first body portion 20 so as to completely enclose the vial 12, with the first body portion 20 and the second body portion 40 being removably engaged with one another via a bayonet connection. This bayonet or like connection between the first and second body portions 20, 40 fixedly connects these portions so that rotational motion imparted to the ratcheting mechanism 60 in the direction of arrow A shown in FIG. 1 is imparted to the transport container 10 generally. Only when the predetermined amount of rotational force is reached to overcome the spring force biasing the pawl elements 84 into the ratchet detents 78 in the ratcheting mechanism 60 will the cap member 62 rotate relative to the second body portion 40. This predetermined amount of force can be preselected to prevent over-tightening of the fluid connection element on the vial 12, namely the connecting tip or end 98, with a corresponding fluid connection element associated with the fluid injection system 100, which could lead to a catastrophic breakage of the connection between these two fluid connection elements and the possible leakage of radioactive fluid. Thus, the at least one pawl element 84 biased into engagement with the at least one ratchet detent 78 defined in the interior surface 70 of the cap member 62 permits rotational engagement of the entire transport container 10 to the docking station 112, but prevents over-torquing of the fluid connection elements between the vial 12 and the fluid injection system 100.

In one exemplary embodiment, the interface portion 110 of the fluid injection mechanism or system 100 includes a fluid connector mechanism 114 comprising a spring-biased collar 116 supporting a mating fluid connector element 118 adapted for a mating connection to the connecting tip or end 98. Thus, the fluid connector element 118 and the mating connecting tip or end 98 may be in the form of inter-engaging threaded luer connectors and like connecting arrangements known in the medical field. The connecting tip or end 98 and the fluid connector element 118 are protected from over-tightening by preselecting or presetting the spring force biasing the pawl elements 84 into the ratchet detents 78 in the ratcheting mechanism 60. Once this predetermined force is overcome by applying excessive rotational force to the cap member 62 of the ratcheting mechanism 60, the pawl elements 84 disengage from their corresponding ratchet detents 78 and this action permits the cap member 62 to rotate relative to the second body portion 40, thereby protecting the connecting tip or end 98 and the fluid connector element 118 from over-tightening or over-torquing.

Figure 11:
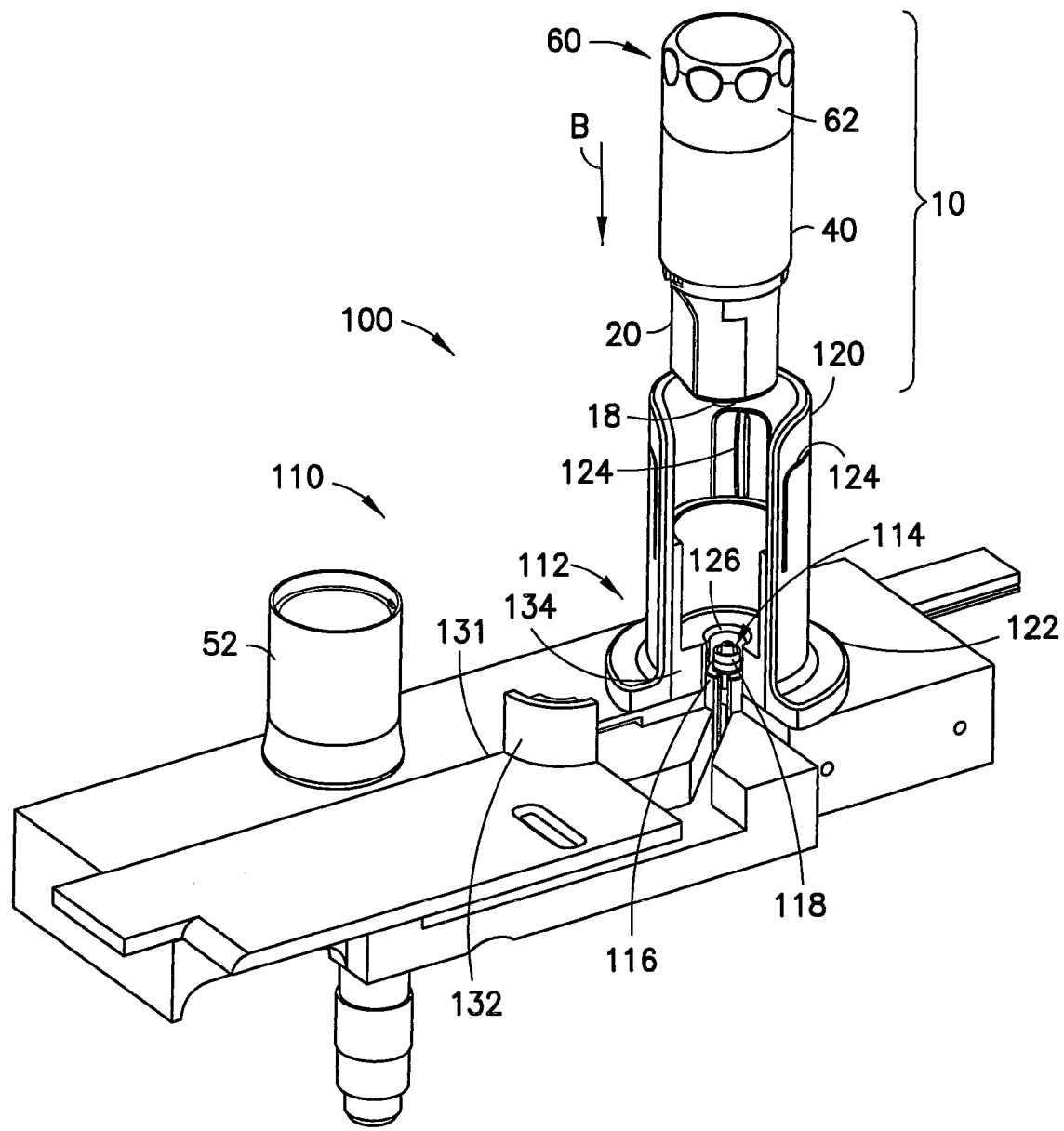
FIGS. 11-13 are perspective views showing an embodiment of a fluid injection system, and further showing, in sequence, steps for connection of the vial transport container shown in FIG. 1 to the fluid injection system to form part thereof.
Figure 13:
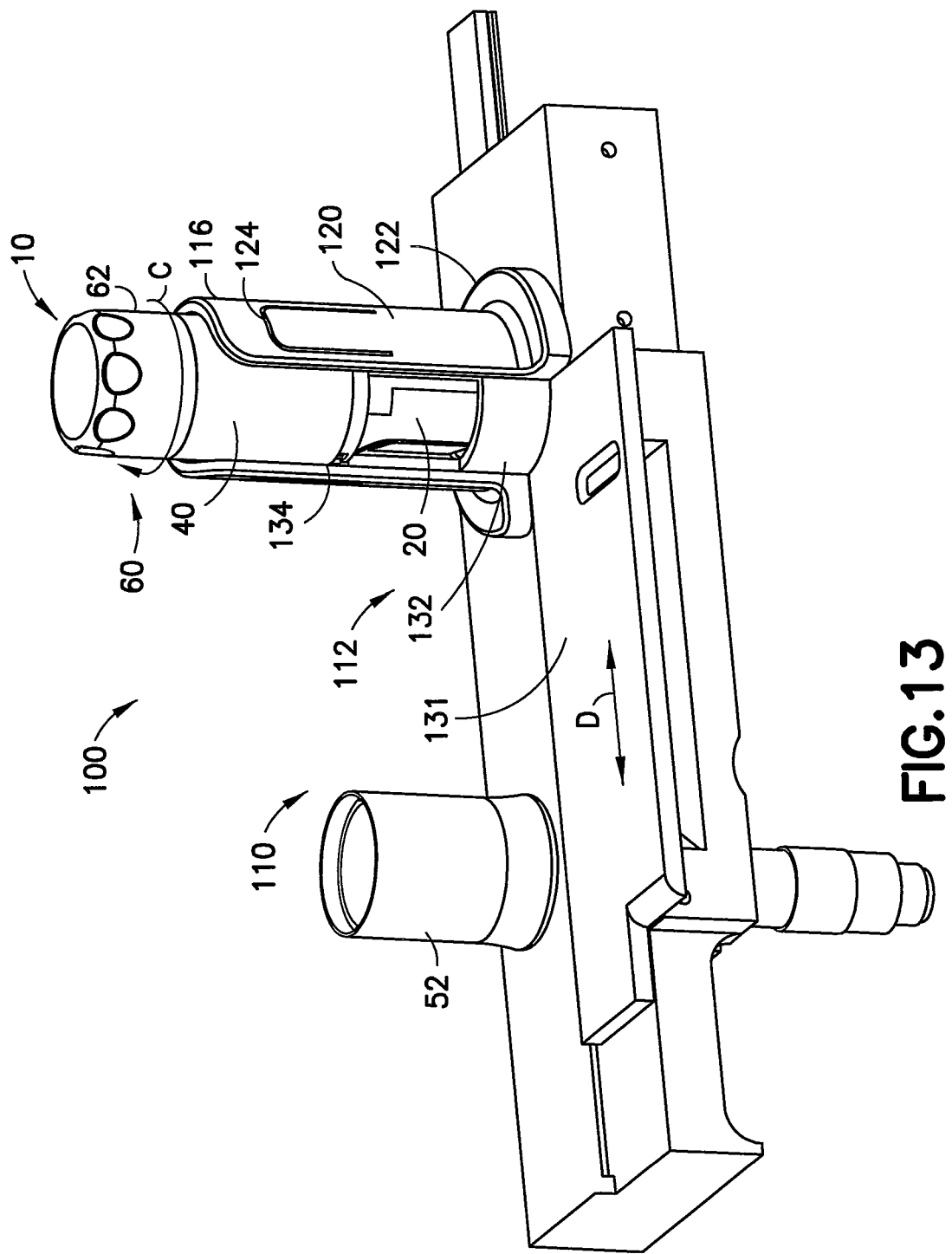
Figure 14:
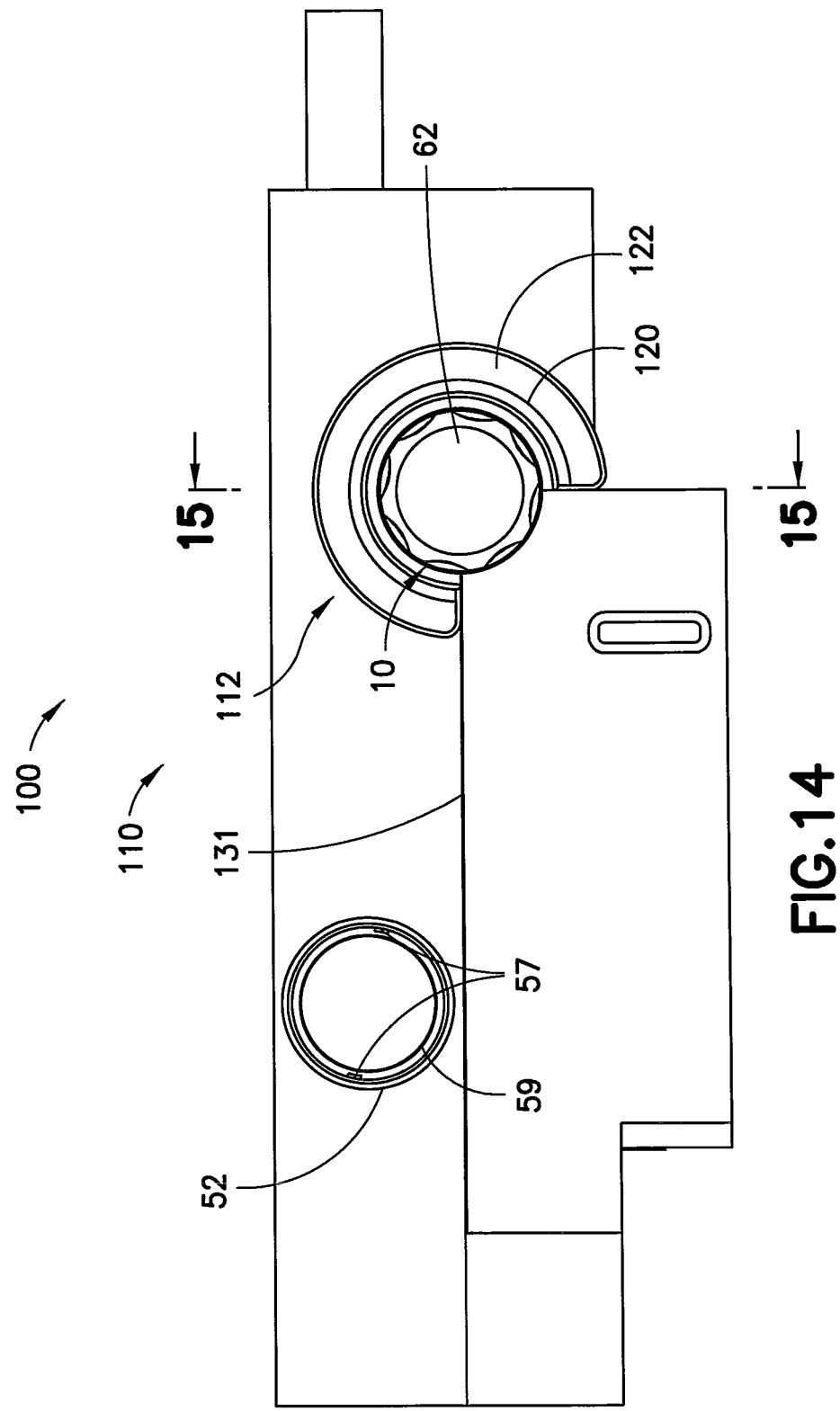
FIG. 14 is a top view of the fluid injection system shown in FIGS. 11-13.
Figure 15:
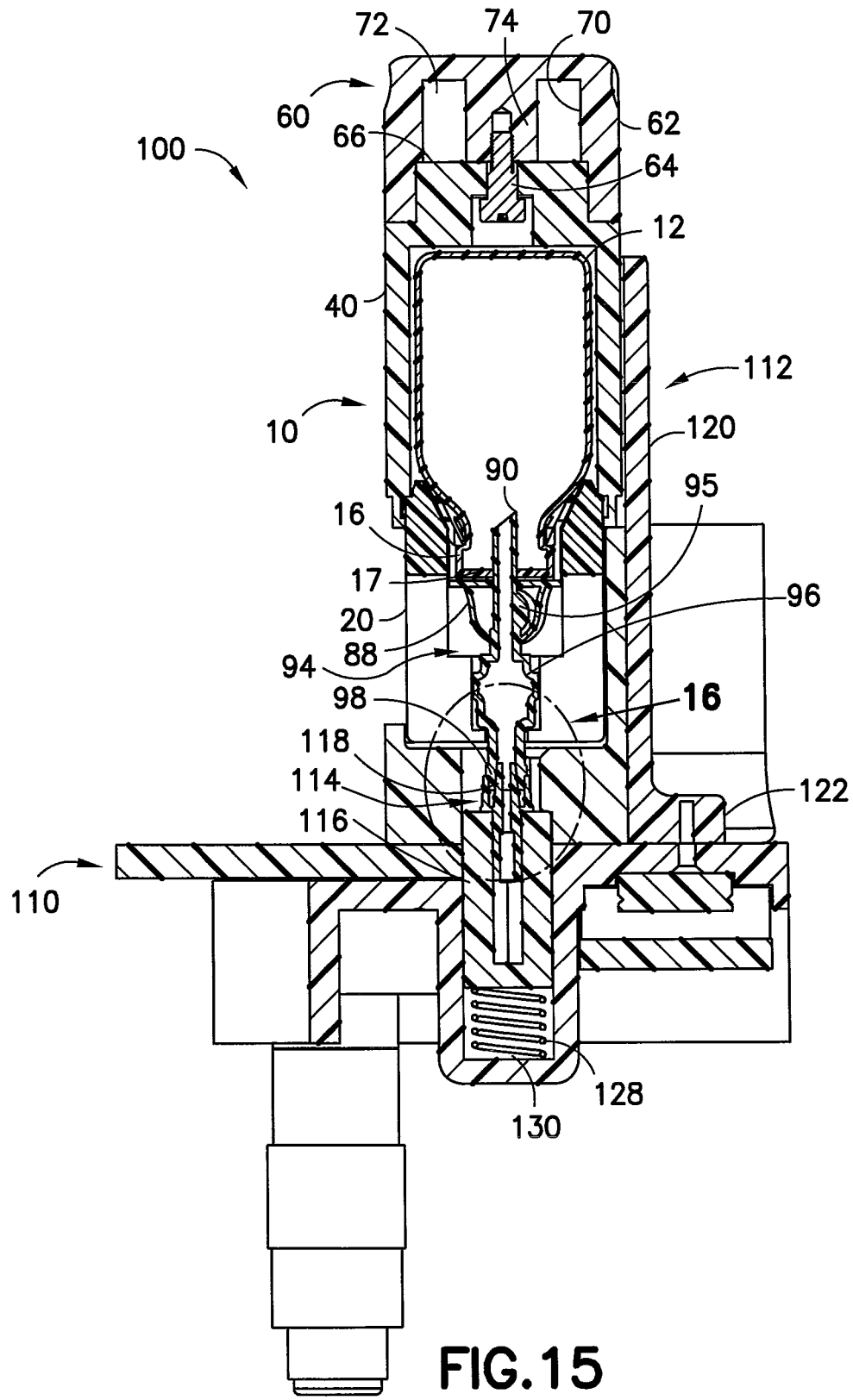
FIG. 15 is cross-sectional view taken along line 15-15 in FIG. 14.
Figure 16:
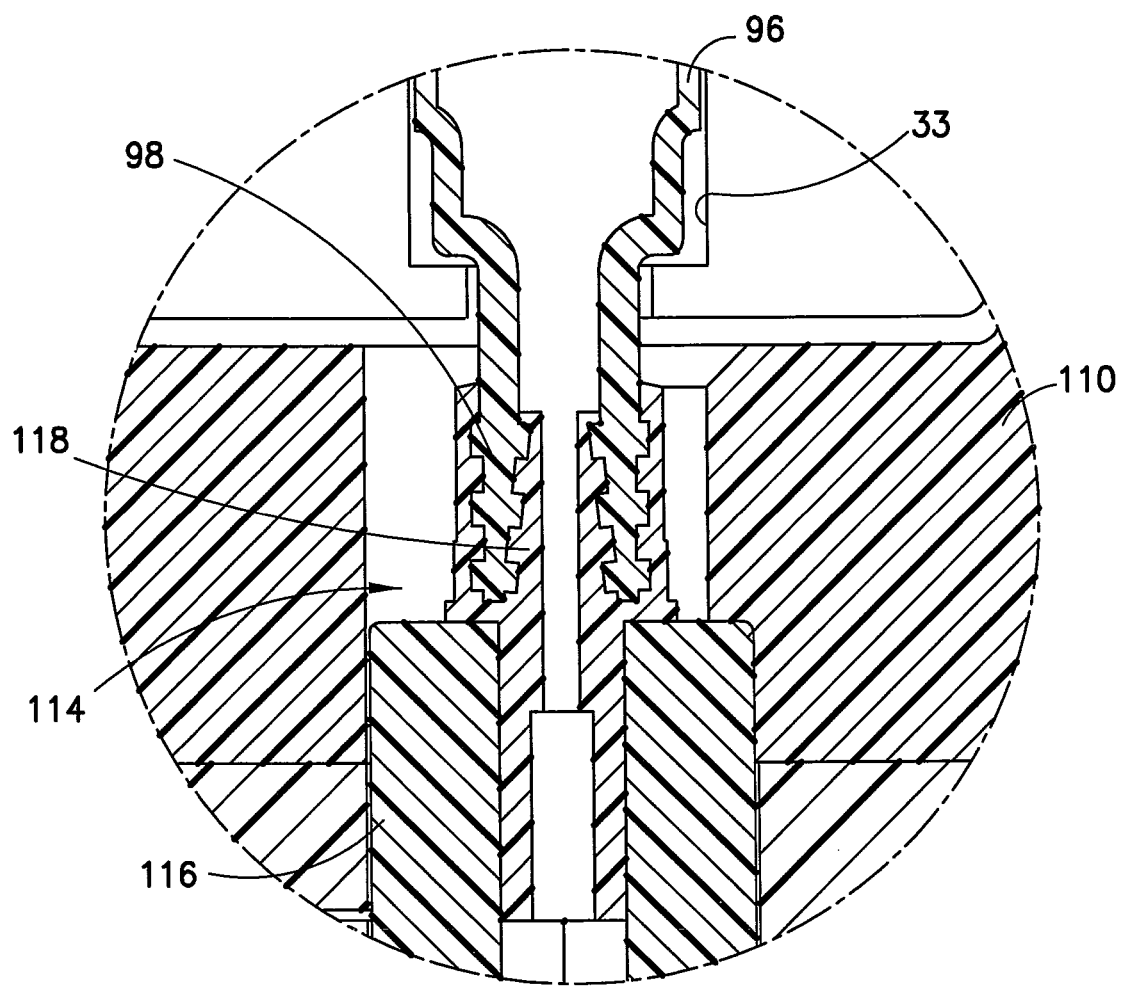
FIG. 16 is a detail view of Detail 16 in FIG. 15.

The docking station 112 may also include a guide collar 120 extending upward from the interface portion 110, which may be, for example, a shielding top plate of the fluid injection mechanism or system 100. The guide collar 120 has a base portion 122 supported to the interface portion 110 and is generally configured to receive the transport container 10 axially into the guide collar 120 from above the interface portion 110. The guide collar 120 includes features to receive and properly align the transport container 10 for fluid connection to the fluid connector mechanism 114. These features include, for example, a plurality of spring arms 124 spaced around the guide collar 120 that are adapted to engage the exterior surface 45 of the second body portion 40 to bias the transport container 10 toward the axial center of the guide collar 120 where the fluid connector mechanism 114 is axially positioned. In this manner, the connecting tip or end 98 and the fluid connector element 118 may be aligned with one another for mating engagement. As shown in FIG. 11, the fluid connector mechanism 114 may be recessed within an opening 126 in the interface portion 110 of the fluid injection mechanism or system 100. The fluid connector element 118 may be positioned on a spring-biased collar 116 as described previously, and the spring-biased collar 116 includes a spring 128 positioned in a chamber 130 provided in the interface portion 110. The spring-biased collar 116 allows the fluid connector element 118 to move axially in the chamber 130 to take up tolerance and ensure that the connecting tip or end 98 and the fluid connector element 118 are in contact before a user tightens this mating connection by rotating the cap member 62 on the transport container 10. As shown in FIG. 13, only the cap member 62 typically extends above the docking station 112 when the transport container 10 is seated therein so only this element is generally available to the user for grasping when tightening the connection between the connecting tip or end 98 and the fluid connector element 118.

Figure 12:
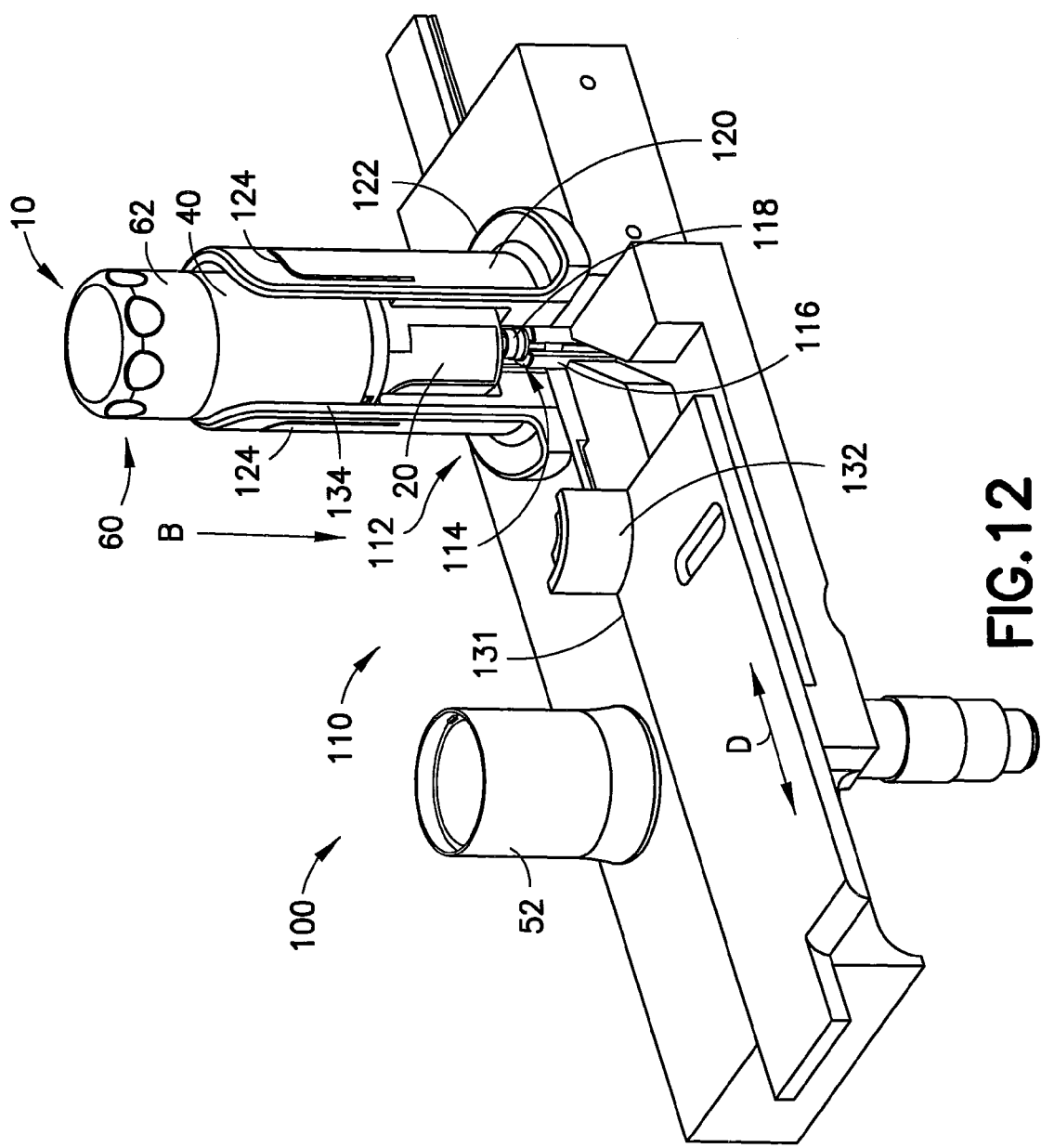

As generally illustrated in sequence in FIGS. 11-13, a user may operatively associate the transport container 10 with the fluid injection mechanism or system 100 by inserting the first body portion 20 of the transport container 10 into the docking station 112. The user may grasp the external detents 77 on the cap member 62 of the ratcheting mechanism 60 and slide the transport container 10 into guide collar 120 in the direction of arrows B shown in FIGS. 11-12. As the transport container 10 enters the guide collar 120, the spring arms 124 contact the exterior surface 45 of the second body portion 40 and align the connecting tip or end 98 extending outward from the opening 32 in the closed distal end 23 of the first body portion 20 with the mating fluid connector element 118 disposed generally along a central axis in the guide collar 120 of the docking station 112. Once the connecting tip or end 98 engages the mating fluid connector element 118, the user may rotate the transport container 10 in the direction of arrow C in FIG. 13 to complete the mating connection between these elements, typically a mating threaded connection. As explained previously, application of rotational force to the cap member 62 of the ratcheting mechanism 60 causes the entire transport container 10, including the first body portion 20 and the second body portion 40, to rotate to complete the fluid connection engagement, typically threaded engagement, between the connecting tip or end 98 and the fluid connector element 118, but only to a predetermined tightness. Accordingly, when tightening the transport container 10 with respect to the docking station 112 by twisting the cap member 62 in the direction of arrow C, the entire transport container 10 rotates within the guide collar 120 of the docking station 112, due to the engagement of the opposing pawl elements 84 in opposing ratchet detents 78 in the interior surface 70 of the cap member 62. However, these features of the ratcheting mechanism 60 permit only a predetermined tightness to be achieved and any additional rotational force applied to the cap member 62 over and above the preselected or predetermined spring or biasing force in the biasing springs 86 of the opposed ratchet pawls 80 by the user in the direction of arrow C causes disengagement of the pawl element 84 from the ratchet detents 78, thereby permitting the cap member 62 to rotate with respect to the second body portion 40. As a result, rotation and, therefore, tightening, of the fluid connection interface between the vial spike adapter 18 and the fluid connector mechanism 114 on the fluid injection system 100 ceases.

The interface portion 110 of the fluid injection system 100 may also optionally include a sliding access member 131 providing access to the fluid connector mechanism 114. As shown, the sliding access member 131 may be slidable, for example, in the direction of arrow D between an open position shown in FIGS. 11-12, and a closed position shown in FIG. 13 to permit access to the chamber 130 containing the spring-biased collar 116. In this manner, the fluid connector element 118 may be easily replaced, for example, if it were a disposable luer connector, and the connection between the transport container 10 and the fluid connector mechanism 114 may be monitored and examined to ensure a proper connection. The sliding access member 131 may comprise an upstanding shield element 132 to shield the user from the fluid connection between the vial spike adapter 18 and the fluid connector mechanism 114. As illustrated, the guide collar 120 may define one open side 134 for improved visibility and the shield element 132 shields the user from direct radiation "shine" from this open side 134 of the guide collar 120. After the transport container 10 is properly connected to fluid injection system 100, the sliding access member 131 may be moved to a closed position to minimize radiation exposure. The sliding access member 131 may enclose a cavity that is used to contain fluid tubing connected to the fluid connector mechanism 114 which conducts fluid from the vial 12 in the transport container 10 to the pumping and fluid delivery components of the fluid injection system 100.

Referring now to FIGS. 17-25, another embodiment of a pharmaceutical transport container 210 for transporting the vial 12 may generally include a first or lower body portion 220 and a second or upper body portion 240 having at least one guide tab and, as shown, two guide tabs, 260 operably associated with the second or upper body portion 240 to engage the pharmaceutical transport container 210 with a fluid injection system, as described in more detail hereinbelow. The transport container 210, including the first body portion 220 and the second body portion 240 having the guide tabs 260 may be constructed of radiation-shielding material. The radiation-shielding material may include machined tungsten, high specific gravity polymer, tungsten powder-nylon blends, and/or combinations thereof, and like radiation-shielding materials. For example, the first body portion 220 and the second body portion 240 may be constructed by injection molding a blend of tungsten powder and nylon.

The first body portion 220 includes a proximal end 221 and a distal end 223 and defines a hollow interior cavity 222 therebetween. The first body portion 220 further has an exterior surface 224 defining a radially-outward extending rim 227. The distal end 223 defines an opening 232 for establishing a fluid connection through the distal end 223, such that the vial 12 disposed in the transport container 210 may be connected to a fluid injection mechanism or system 300, as described herein in connection with FIGS. 26-28, for delivery of a pharmaceutical or radiopharmaceutical to a patient. For example, the transport container 210, as described herein, and like transport container 10 and fluid injection mechanism 100 described above with respect to FIGS. 1-16, may be used in conjunction with a molecular imaging infusion system, such as the Intego™ PET Infusion System sold by Medrad, Inc. of Indianola, Pa., and the fluid injection mechanism or system 300 described herein in connection with FIGS. 26-28 may be the Intego™ PET Infusion System and like systems.

Figure 22:
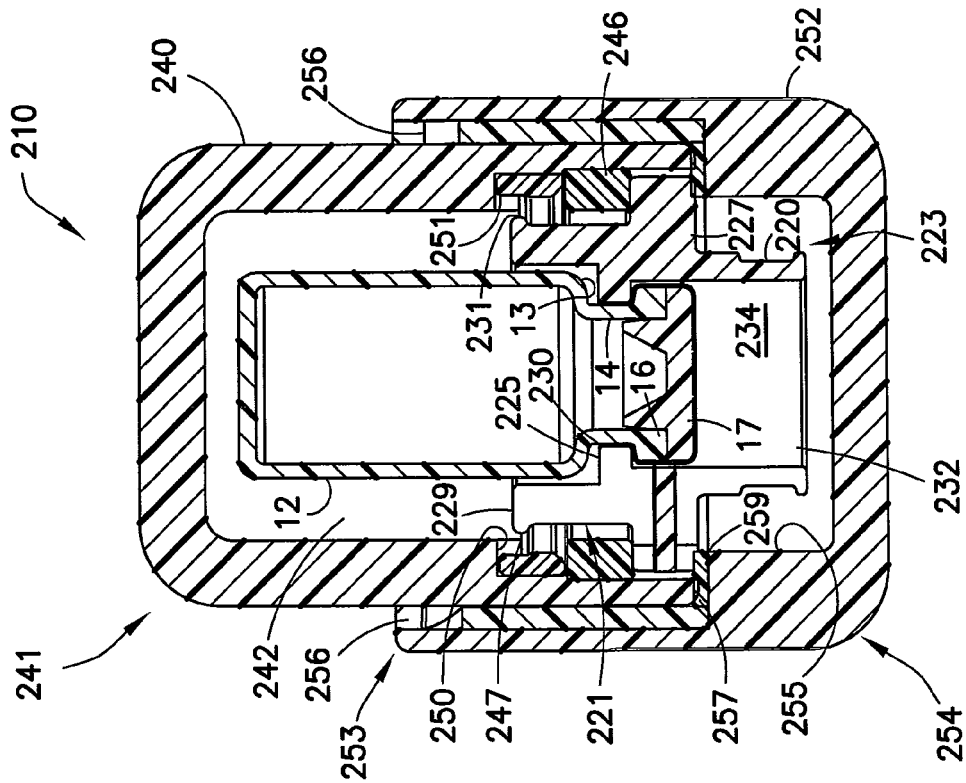
FIG. 22 is a cross-sectional view taken along line 22-22 in FIG. 20.
Figure 23:
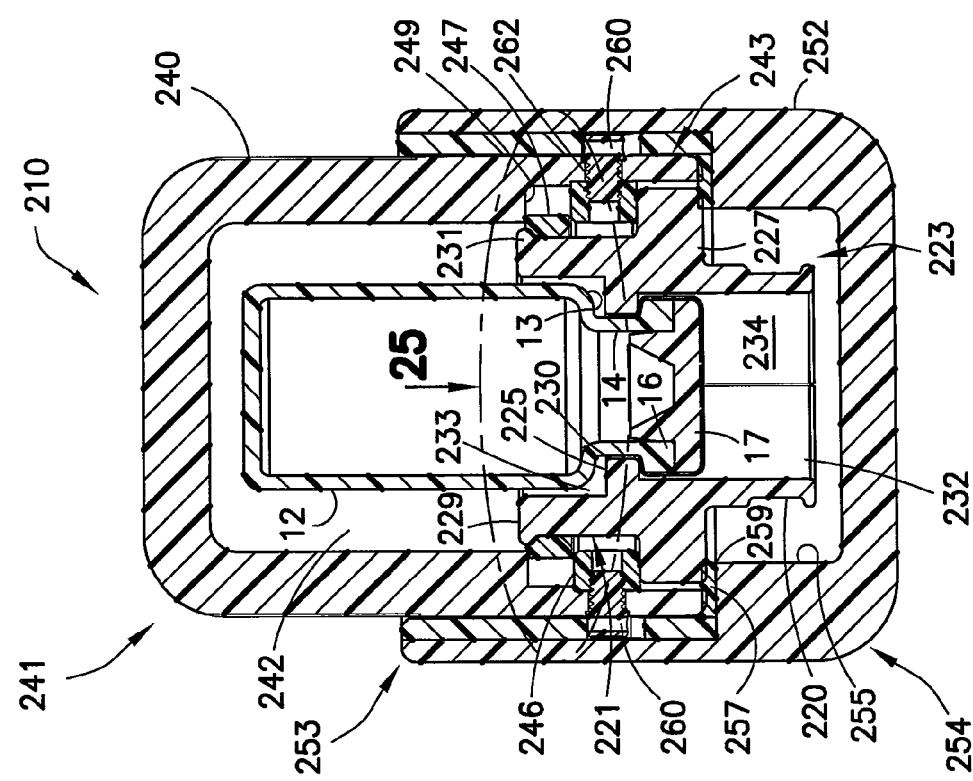
FIG. 23 is a cross-sectional view taken along line 23-23 in FIG. 20.

The second body portion 240 has a closed proximal end 241 and an open distal end 243. The second body portion 240 is typically hollow to define a hollow interior cavity 242, as best shown in FIGS. 19 and 22-23, having an interior surface 244. The second body portion 240 further comprises an exterior surface 245. Generally, the first body portion 220 and the second body portion 240 are configured to cooperatively receive, enclose, and support the vial 12. As described above, the vial 12 has a tapered end portion 13 that narrows to form a neck 14 and a cap end 16 sealed with a conventionally puncturable vial stopper 17. The neck 14 is defined intermediately between the tapered end portion 13 and the cap end 16. The vial 12 may be filled with a pharmaceutical to be delivered to a patient or, in particular, a radiopharmaceutical for use in molecular imaging procedures. Also, as explained above, the vial 12 may optionally be an ISO compliant bulk vial and may range, for example, between 10 and 30 mL in volume, and the vial stopper 17 puncturable to provide a fluid connection point to a fluid injection mechanism or system, such as fluid injection system 300.

Figure 17:
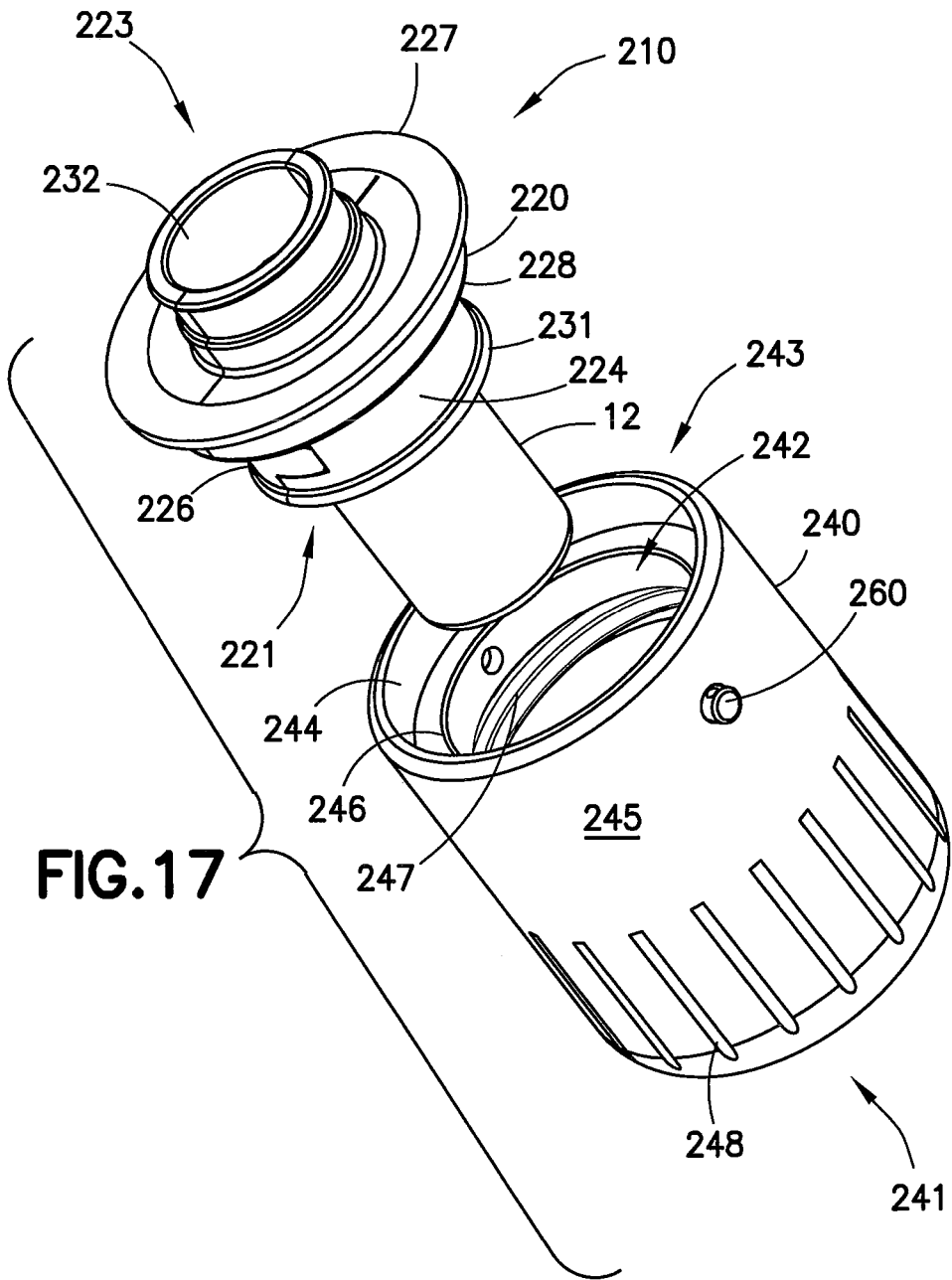
FIG. 17 is an exploded perspective view of another embodiment of a vial transport container.
Figure 18A:
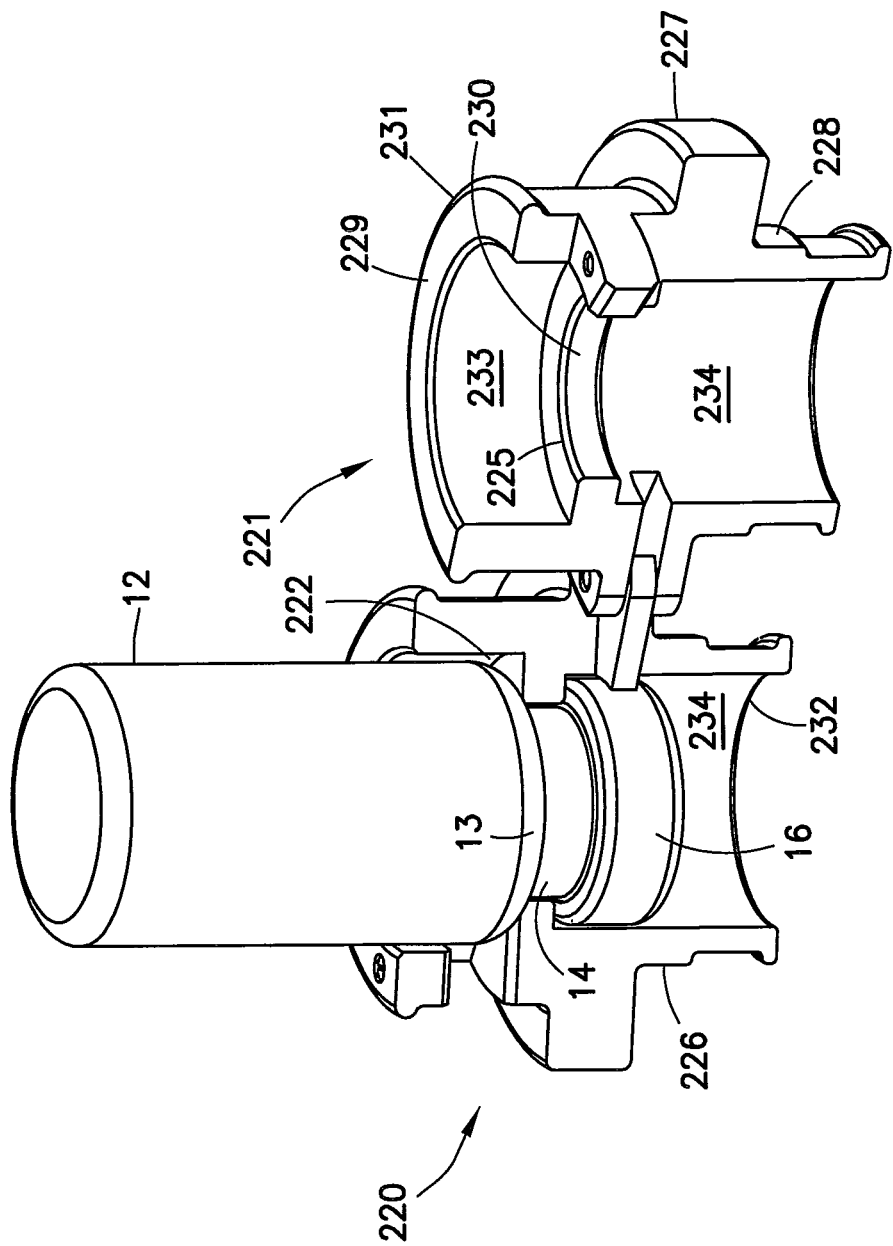
FIG. 18A is a perspective view of a portion of the vial transport container of FIG. 17 and showing a vial associated with the shown portion of the vial transport container.

As best shown in FIG. 18A, the first body portion 220 may be constructed as a clamshell member. Thus, the clamshell first body portion 220 may be divided into a first half or portion 226 and a second half or portion 228, with the first half 226 and the second half 228 being hingedly connected with each other. In this manner, the first body portion 220 may be moved between a closed position as shown in FIG. 17, and an open position as shown in FIG. 18A. In the open position, the vial 12 may be supported by one of the halves during the loading process, such as the first half or portion 226 as shown in FIG. 18A. The second half or portion 228 may then be hingedly moved to abut the first half or portion 226 to enclose at least the discharge portion of the vial 12 (e.g., the tapered end portion 13, the neck 14, and the cap end 16 sealed with vial stopper 17). By engaging the discharge portion, the first body portion 220 can engage any size vial having a cap 16 and neck 14.

Referring to FIGS. 18A and 22-23, the first body portion 220 defines an interior cavity 222 which accommodates the cap end 16 enclosed by the vial stopper 17, and the tapered end portion 13 of the vial 12. The interior cavity 222 comprises a proximal chamber 233 that is shaped to accommodate at least a portion of the body of the vial 12 and the tapered end portion 13, and a distal chamber 234 which accommodates the cap end 16 of the vial 12. The first body portion 220 also includes a radially-inward extending rim 225 extending into the interior cavity separating the proximal chamber 233 and the distal chamber 234 and defining an opening 230 therethrough to engage the neck 14 of the vial 12. The rim 225 may further support the tapered end portion 13 of the vial 12 as shown in FIG. 18A. When the first body portion 220 is moved to the closed position, the rim 225 surrounds and engages the neck 14 of the vial 12, with the neck 14 extending through the opening 230 such that the top or proximal chamber 233 generally receives the body of the vial 12 and the tapered end portion 13, while the bottom or distal chamber 234 generally receives the cap end 16 of the vial 12 including vial stopper 17. Because the first body portion 220 engages vial 12 at neck 14, any vial will be properly positioned and aligned in first body portion 220 regardless of the size of the vial body.

The first body portion 220 is removably engageable with the second body portion 240. As shown, the open distal end 243 of the second body portion 240 may engage and mate with the open proximal end 221 of the first body portion 220, such that the open proximal end 221 of the first body portion 220 is received into the open distal end 243 of the second body portion 240. However, this specific configuration may be reversed if so desired. The open proximal end 221 of the first body portion 220 includes a top surface or wall 229 defining a radially-outward extending lip or rim 231. When the open proximal end 221 of the first body portion 220 is mated with the open distal end 243 of the second body portion 240, the top surface 229, including the radially-outward extending lip or rim 231, is received into the open distal end 243 of the second body portion 240.

Figure 18B:
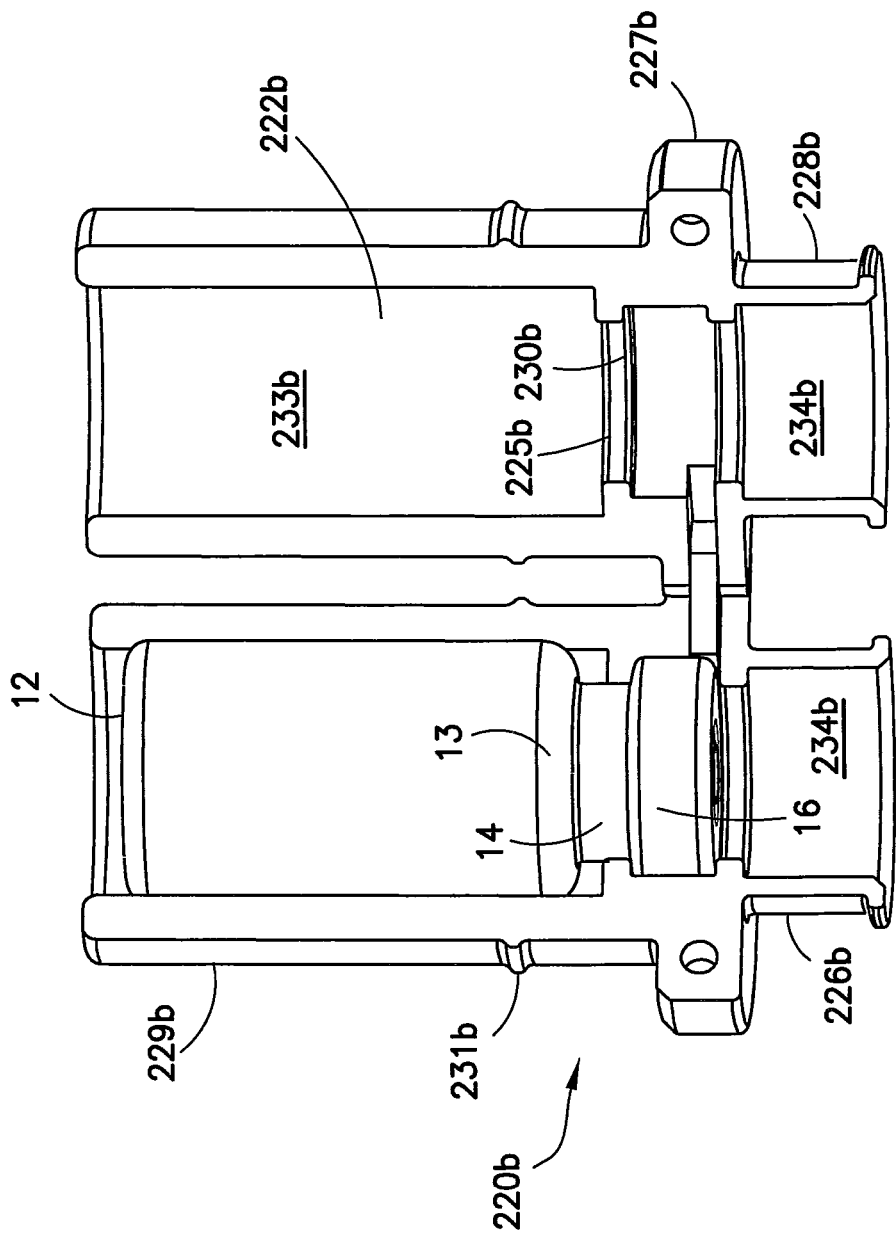
FIG. 18B is a perspective view of an alternative embodiment of the portion of the vial transport container shown in FIG. 18A.

Referring now to FIG. 18B, an alternative embodiment of the first body portion 220b may include a proximally extending wall, or shroud, 229b for circumferentially enclosing the body of the vial 12. As shown, first body portion 220b may be constructed as a clamshell member, similar to first body portions 20, 220, discussed above. Thus, the clamshell first body portion 220b may be divided into a first half or portion 226b and a second half or portion 228b, with the first half 226b and the second half 228b being hingedly connected with each other. In this manner, the first body portion 220b may be moved between a closed position and an open position. In the open position, the vial 12 may be supported by one of the halves during the loading process, such as the first half or portion 226b as shown in FIG. 18B. The second half or portion 228b may then be hingedly moved to abut the first half or portion 226b to enclose at least the discharge portion of the vial 12 (e.g., the tapered end portion 13, the neck 14, and the cap end 16 sealed with vial stopper 17). By engaging the discharge portion, the first body portion 220 can engage any size vial having a cap 16 and neck 14.

The first body portion 220b further defines an interior cavity 222b which accommodates the cap end 16 enclosed by the vial stopper 17, and the tapered end portion 13 of the vial 12. The interior cavity 222b comprises a proximal chamber 233b that is shaped to accommodate at least a portion of the body of the vial 12 and the tapered end portion 13, and a distal chamber 234b which accommodates the cap end 16 of the vial 12. The first body portion 220b also includes a radially-inward extending rim 225b extending into the interior cavity separating the proximal chamber 233b and the distal chamber 234b and defining an opening 230b therethrough to engage the neck 14 of the vial 12. The rim 225b may further support the tapered end portion 13 of the vial 12 as shown in FIG. 18B. When the first body portion 220b is moved to the closed position, the rim 225b surrounds and engages the neck 14 of the vial 12, with the neck 14 extending through the opening 230b such that the top or proximal chamber 233b generally receives the body of the vial 12 and the tapered end portion 13, while the bottom or distal chamber 234b generally receives the cap end 16 of the vial 12 including vial stopper 17. Because the first body portion 220b engages vial 12 at neck 14, any vial will be properly positioned and aligned in first body portion 220b regardless of the size of the vial body.

Like first body portion 220, first body portion 220b is removably engageable with the second body portion 240. However, unlike first body portions 20, 220, first body portion 220b further includes the proximally extending wall or shroud 229b, which completely surrounds the body of the vial 12. The proximally extending wall, or shroud, 229b is configured to receive and surround the body of the vial 12 and is receivable within the interior cavity 242 of the second body portion 240. The open distal end 243 of the second body portion 240 may engage and mate with the proximally extending wall, or shroud, 229b, such that the proximally extending wall, or shroud, 229b and radially-outward extending lip or rim 231b is received into the interior cavity 242 of the second body portion 240. The wall 229b completely surrounds the vial 12 protecting the vial 12 from potential breakage. Further, when the first body portion 220b is inserted into second body portion 240 by a user, the wall 229b may provide additional radiation-shielding protection for the user. With the exception of proximally extending wall or shroud 229b, first body portion 220b functions and operates, in conjunction with second body portion 240 identically to first body portion 210, as described herein.

Figure 24:
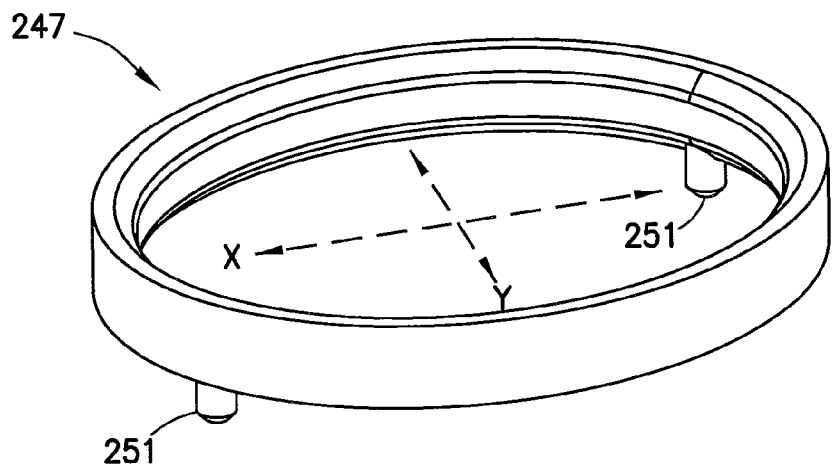
FIG. 24 is a perspective view of a flexible ring used in the vial transport container of FIG. 17.
Figure 25:
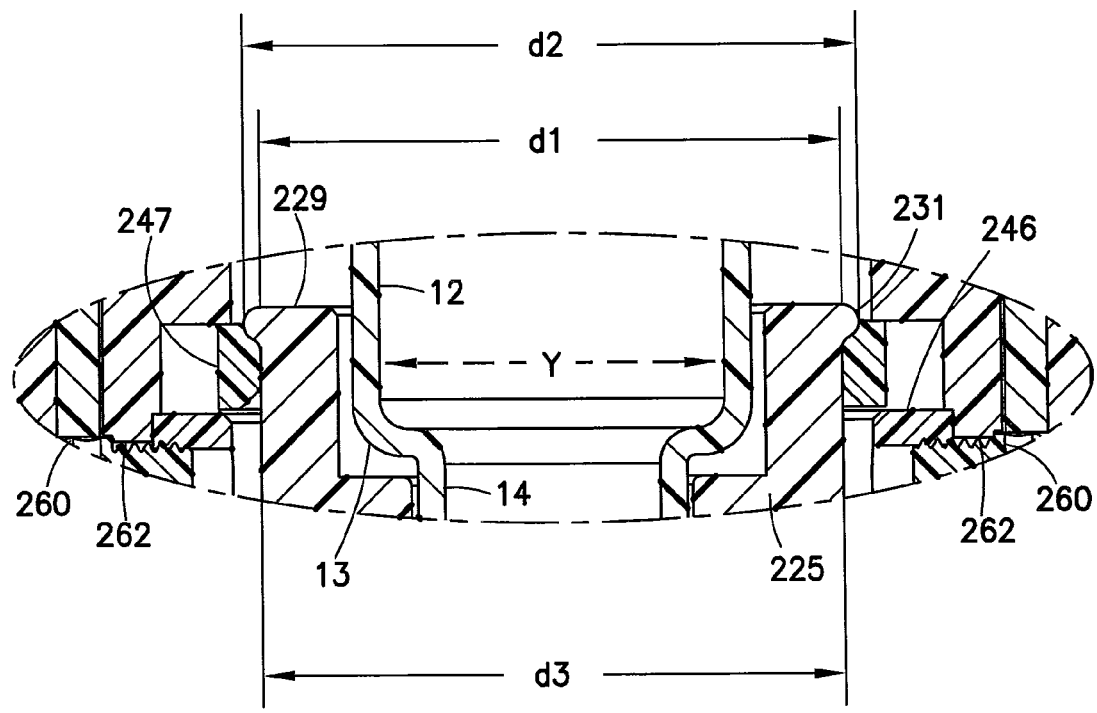
FIG. 25 is a detail view of Detail 25 in FIG. 22.

As shown in FIGS. 19 and 22-25, the first body portion 220 and the second body portion 240 may be secured in removable engagement by a flexible ring 247 that is flexible between a relaxed state and radially-outward extending deformed state. The flexible ring 247 is positioned in the interior cavity 242 of the second body portion 240. The second body portion 240 includes a retaining ring 246 positioned in the interior cavity 242 and an interior shoulder 249 to retain the flexible ring 247 therein. The flexible ring 247 is positioned between the retaining ring 246 and the interior shoulder 249. The interior shoulder 249 further includes ring receiving pockets 250 positioned opposite each other configured to receive flex ring extensions 251 positioned on flexible ring 247. The engagement of flex ring extensions 251 with receiving pockets 250 aids in preventing movement of flexible ring 247 within interior cavity 242. As illustrated, the flexible ring 247 may be substantially elliptical having a major axis X and a minor axis Y. Referring specifically to FIGS. 24 and 25, in the relaxed state, the minor axis Y of the flexible ring 247 defines an inside distance d1 that is smaller than the outside diameter d2 of radially-outward extending lip or rim 231, or in the case of the first body portion 220b, rim 231b of proximally extending wall or shroud 229b, and substantially equal to the outside diameter d3 of the proximal end 221. Because d2 is greater than d1, when a user inserts first body portion 220 into interior cavity 242 of second body portion 240, radially-outward extending rim 231 or rim 231b causes flexible ring 247 to extend and deform radially, thereby allowing the first body portion proximal end 221 to be inserted therethrough. Although as illustrated, flexible ring 247 is elliptically-shaped, those skilled in the art will recognize radial deformation to mean any deformation of flexible ring 247 in the direction of axes X, Y because such deformation is radial relative to first body portion 220. Moreover, those skilled in the art will further recognize that flexible ring 247 need not be elliptical, and may take any other suitable equivalent form, such as a circular ring. Due to the flexible nature of flexible ring 247, once rim 231 is inserted therethrough, flexible ring 247 will return from a radially-outward deformed state to the relaxed state, wherein d1 is substantially equal to d2. Thus, the flexible ring 247 will engage the proximal end 221 of first body portion 220 along the minor axis Y, as best shown in FIGS. 22 and 25. As shown in FIG. 23, along the major axis X, there is a gap 237 between flexible ring 247 and proximal end 223 of first body portion 220. Those skilled in the art will recognize that other suitable and equivalent removable or detachable connecting arrangements may be substituted for the flexible ring-type connection shown in the Figures, as this specific connection arrangement is exemplary and not intended to be limiting. For example, the connection may include the various flexible ring-type connections described in U.S. Pat. No. 7,419,478 to Reilly et al., which is hereby incorporated by reference.

As discussed above, the first body portion 220 is removably engaged with the second body portion 240 via the flexible ring 247, which is positioned between the interior shoulder 249 and retaining ring 246. When the first body portion 220 is engaged with the second body portion 240, the retaining ring 246 also abuts and overlaps the radially-outward extending rim 227 between proximal and distal ends 221, 223 of first body portion 220 on a side opposite the flexible ring 247. This overlapping engagement prevents radioactive "shine" from emitting outward from the transport container 210 at the interface between the first body portion 220 and the second body portion 240 should the vial 12 be filled with a radiopharmaceutical fluid.

Referring to FIGS. 20-23, the transport container 210 is shown including an optional end cap 252. In this embodiment, the end cap 252 may be positioned over the first body portion 220, including the opening 232. The end cap 252 includes an open proximal end 253 and a closed distal end 254 to define a receiving chamber 255 to receive at least the first body portion 220 therein. As shown, the opening 232 allows the vial cap end 16 including vial stopper 17 to be exposed, while the rest of the vial 12 is enclosed within first body portion 220 and second body portion 240. Since the vial 12 may be filled with a radiopharmaceutical, the opening 232 presents a radiation exposure risk to a user, even though the first body portion 220 and the second body portion 240 both typically include radiation-shielding material. Therefore, like end cap 52 discussed above and with respect to FIGS. 9-10, the end cap 252 also includes radiation-shielding material, such as those materials discussed previously in connection with the first body portion 220 and the second body portion 240. The end cap 252 is generally positioned over the first body portion 220 and/or second body portion 240 during transportation of the transport container 210. The end cap 252 may be removably connected and engageable with the second body portion 240. For example, the end cap 252 may be removably connected to the second body portion 40 via at least one helical guide slot 256 or, as shown, two guide slots 256. In this regard, at least one guide tab 260 and, as shown, the two guide tabs 260 are engageable within the guide slots 256. Alternatively, the end cap 252 and first body portion 220 or second body portion 240 may define opposing threads for engagement. The guide tabs 260 extend radially-outward from the exterior surface 245 of the second body portion 240. As illustrated in FIGS. 22-23, the guide tabs 260 extend through the exterior surface 245 of second body portion 240 and into the retaining ring 246 in interior cavity 242. In this manner, the guide tabs 260 may secure the retaining ring 246 against the interior surface 244 in the interior cavity 242 of the second body portion 240. As best shown in FIG. 25, the guide tabs 260 may be threadably engaged with retaining ring 246, with guide tabs 260 and retaining ring 246 having opposing threads 262. The helical guide slots 256 are defined on an interior surface 258 of the end cap 252 in receiving chamber 255. In this arrangement, the guide tabs 260 are inserted into and engage with the guide slots 256 and track therethrough, such that the transport container 210 may be rotated about the end cap 252 and translate axially to be inserted therein. The end cap 252 includes an abutment rim or flange 259 extending radially-inward in receiving chamber 255 at the distal end 254. The rim 259 may act as a stop for engagement with the distal end 243 of the second body portion 240. The end cap 252 may also include a gasket seal 257 positioned proximally on rim 259 between the second body portion 240 and the end cap 252 to provide a seal therebetween in the event of breakage and/or leakage of the vial 12.

Figure 26A:
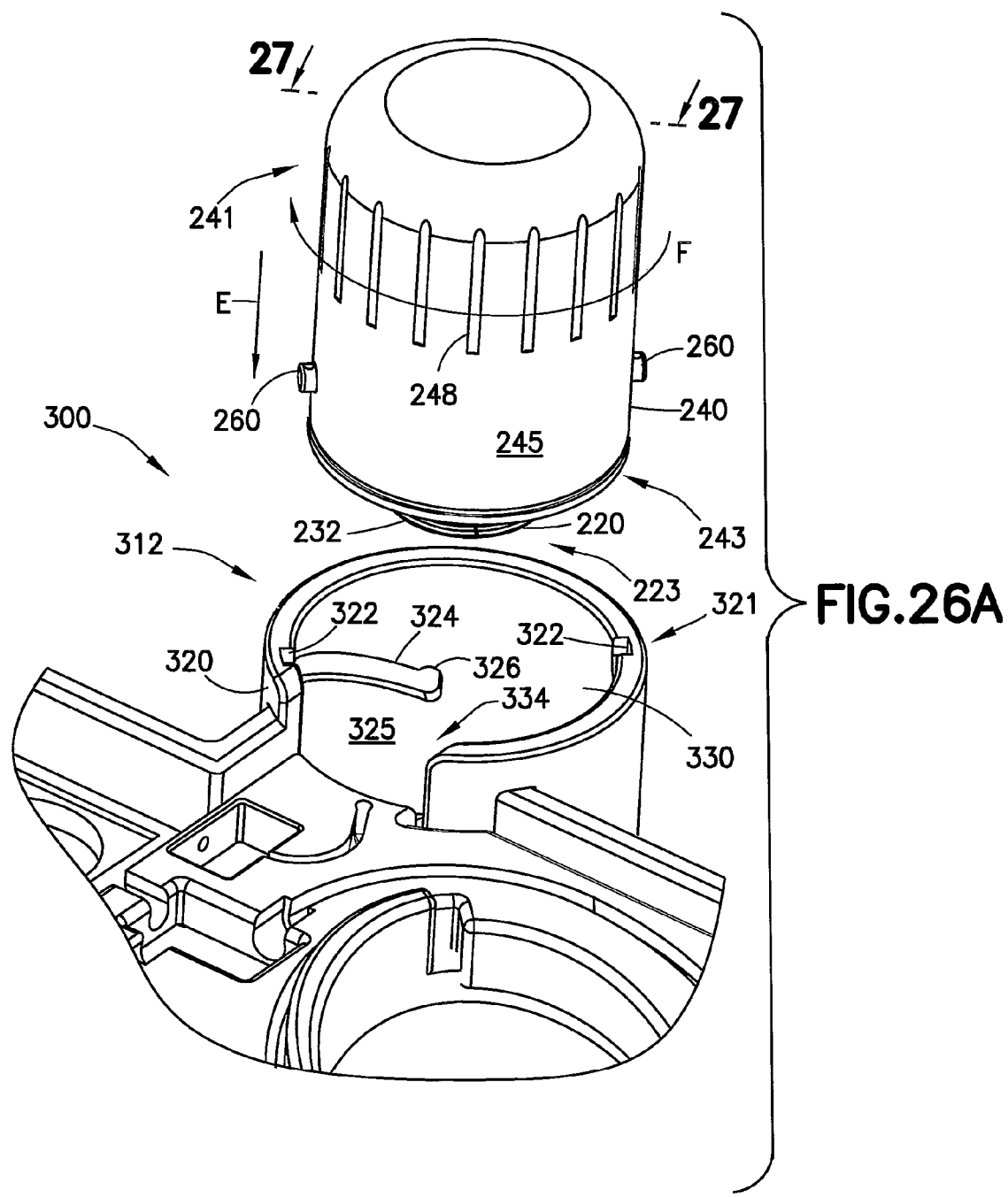
FIG. 26A is a perspective and partially exploded view of a fluid injection system incorporating the vial transport container shown in FIG. 17.
Figure 26B:
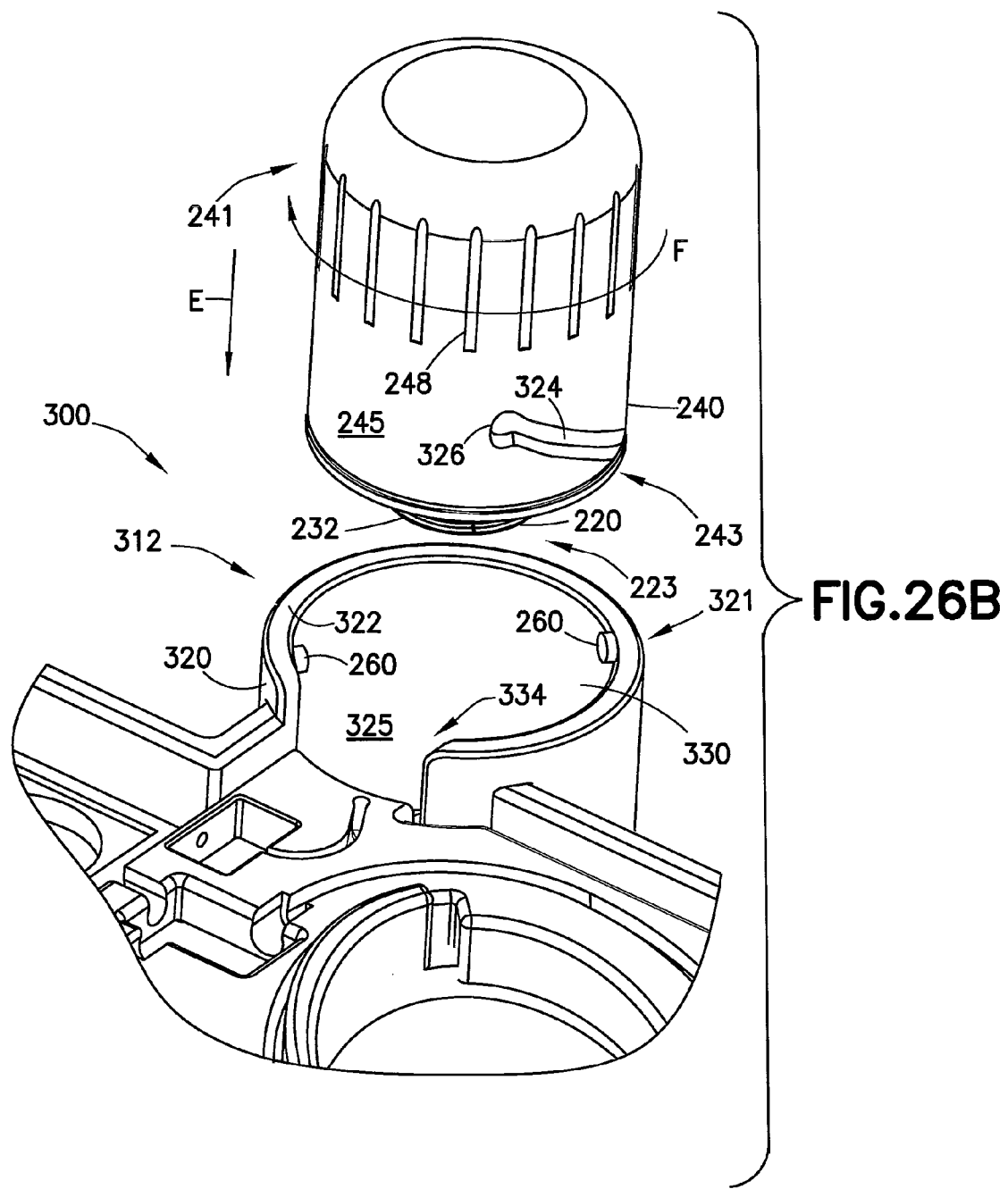
FIG. 26B is an alternative configuration of the fluid injection system of FIG. 26A.
Figure 27:
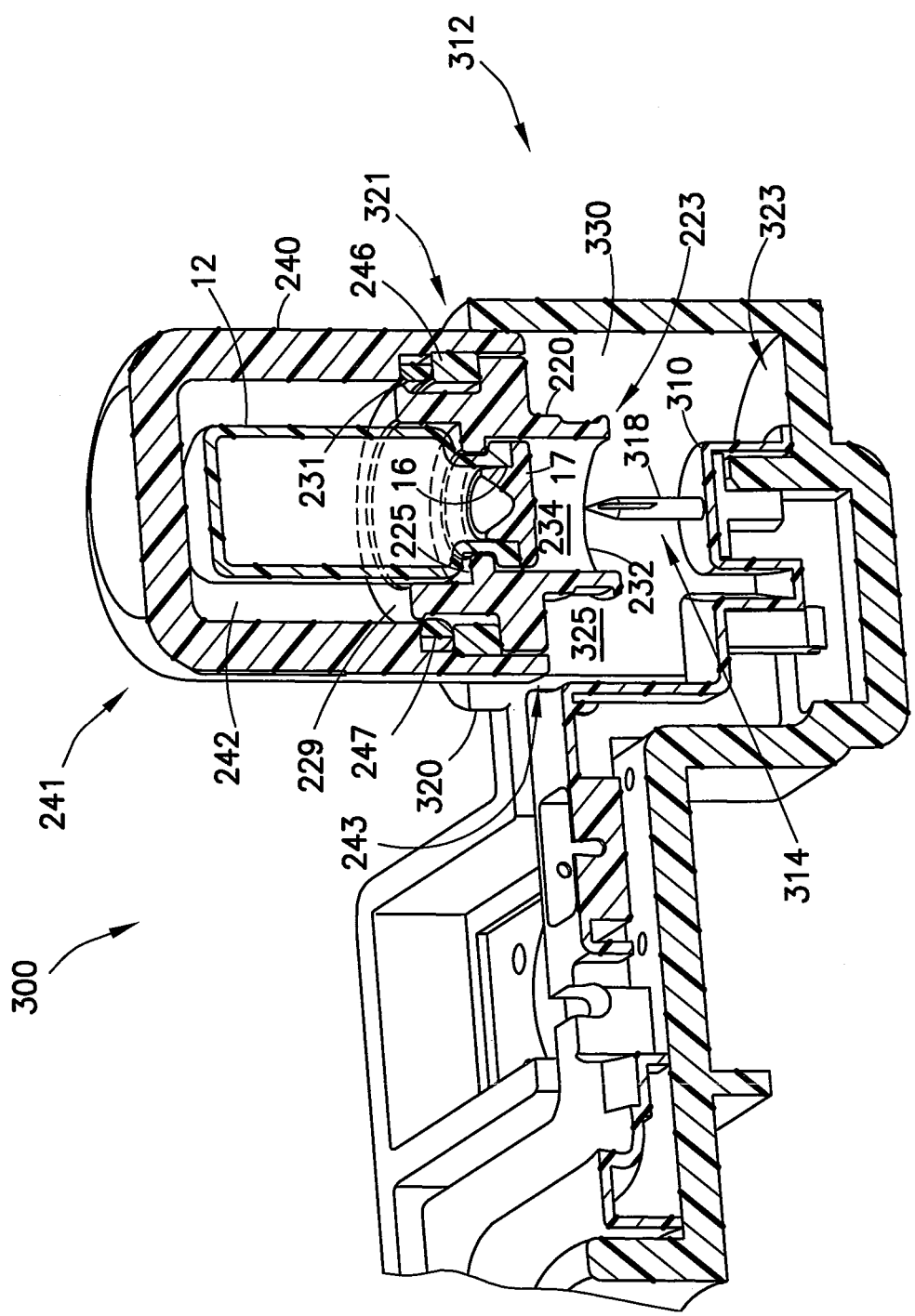
FIGS. 27-28 are cross-sectional views taken along line 27-27 of FIG. 26, and further showing, in sequence, steps for connection of the vial transport container shown in FIG. 17 to the fluid injection system shown in FIG. 26.
Figure 28:
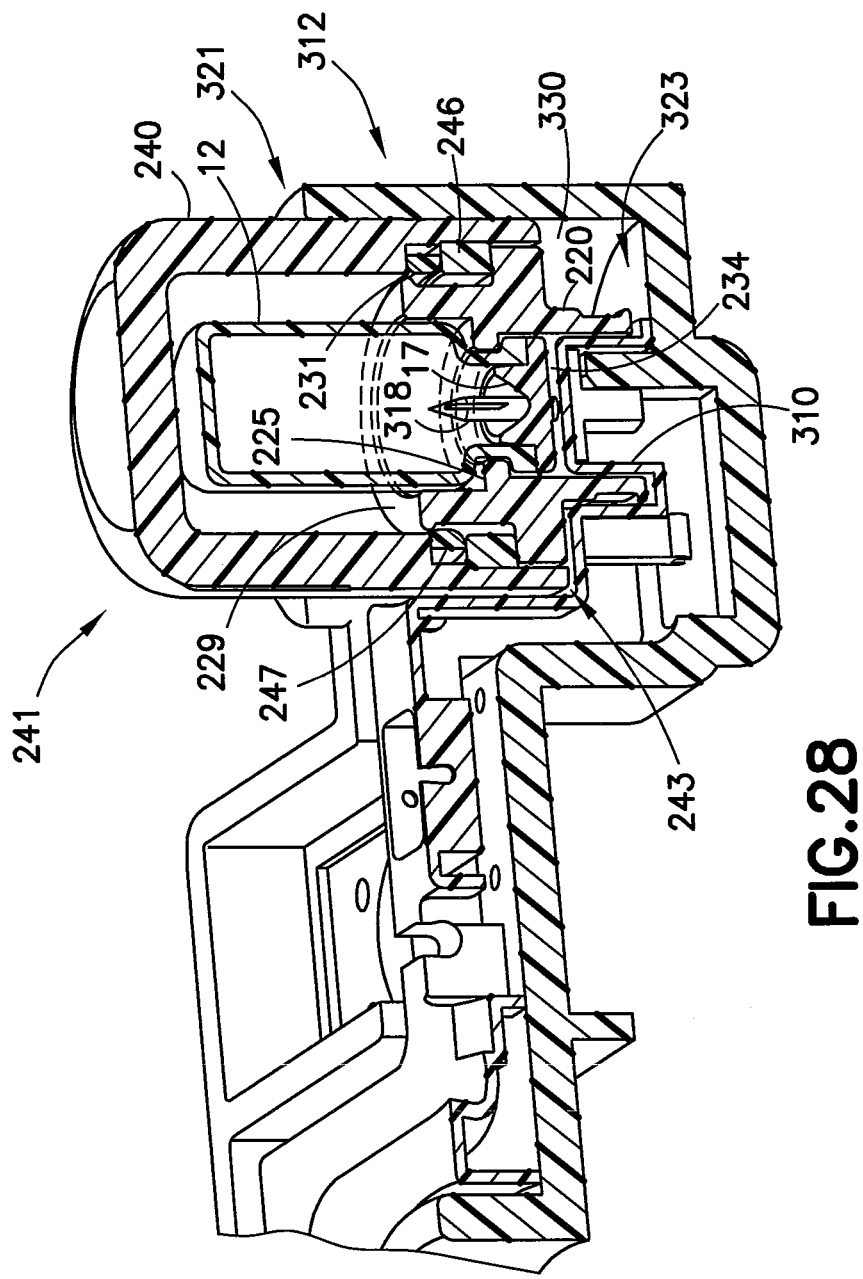

Referring additionally to FIGS. 26-28, a pharmaceutical fluid injection mechanism or system 300 is generally shown. The fluid injection mechanism or system 300 comprises a docking station 312 having an interface portion 310 for the pharmaceutical transport container 210, described hereinabove. As explained previously, the first body portion 220 generally supports the vial 12. In this embodiment, the fluid connection element for the transport container 210 is the vial stopper 17, which is generally puncturable by a needle cannula, vial spike, or similar fluid connector. The docking station 312 is adapted to receive the transport container 210 so that the vial 12 can be operably engaged with the fluid conducting components (not shown) of the fluid injection system 300 which could, for example, take the form of the Intego™ PET Infusion System sold by Medrad, Inc. of Indianola, Pa. As further described previously, the second body portion 240 cooperates with the first body portion 220 so as to completely enclose the vial 12, with the first body portion 220 and the second body portion 240 being removably engaged with one another via the flexible ring 247.

In one exemplary embodiment, the interface portion 310 of the docking station 312 of the fluid injection mechanism or system 300 includes a fluid connector element 314 disposed therein and comprising a piercing connector element, such as a vial spike 318, to establish a fluid connection with the remainder of the fluid injection system 300. Thus, when the pharmaceutical transport container 210 is received within the docking station 312, the vial spike 318 of fluid connector element 314 will puncture vial stopper 17, thereby providing a fluid connection between the interior of the vial 12 and the injection system 300.

Like docking station 112, described above, docking station 312 may also include a guide collar 320 extending upward from the interface portion 310. The guide collar 320 has an open proximal end 321 and a base portion 323 supporting the interface portion 310, and defines an interior receiving chamber 330 generally configured to receive the transport container 210 axially into the guide collar 320 from above the interface portion 310. In this embodiment, the interface portion 310 may be a column extending upward from the base portion 323 of the guide collar 320, and from which the vial spike 318 projects. The interface portion 310 is receivable within the distal chamber 234 of the first body portion 220. The guide collar 320 includes features to receive and properly align the transport container 210 for fluid connection to the vial spike 318. As best illustrated in FIG. 26, these features include, for example, at least one guide slot 324 and, as shown, two guide slots 324, defined on an interior surface 325 of guide collar 320 to engage the guide tabs 260 of second body portion 240. As illustrated, the guide slots 324 are helical. In this manner, the guide slots 324 are configured to engage the guide tabs 260 on the second body portion 240 to rotate the pharmaceutical transport container 210 together with the first and second body portions 220, 240 within the docking station 312 and thereby translate the transport container 210 axially in the direction of the interface portion 310. The guide slots 324 include entrance points 322 at the proximal end 321 of guide collar 320 and end pockets 326 to receive guide tabs 260 when the fluid connection between vial 12 and the injection system 300 has been established. Alternatively, the guide collar 320 and the first body portion 220 or second body portion 240 may define opposing threads for engaging the transport container 210 to the docking station 312.

As shown in FIGS. 26-28, a user may operatively associate the transport container 210 with the fluid injection mechanism or system 300 by inserting the first and second body portions 220, 240 of the transport container 210 into the docking station 312. The user may grasp the external surface 245, which may include tactile feedback detents 248, and insert the transport container 210 into guide collar 320 in the direction of arrows E shown in FIG. 26 by sliding guide tabs 260 into entrance points 322 of guide slots 324. The user can then rotate the transport container 210 in the direction of arrow F. Because the guide slots 324 are helically shaped, as the user rotates the transport container 210, the guide tabs 260 will slide in guide slots 324 translating the transport container axially through guide collar 320 in the direction of arrow E. As the transport container 210 is translated axially, the vial spike 318 of the interface portion 310 of docking station 312 will automatically puncture the vial stopper 17 of vial 12 thereby establishing a fluid connection between the interior of the vial 12 and the injection systems 300. The end pockets 326 are positioned on the interior surface 325 such that a user cannot insert the transport container 210 beyond a predetermined or pre-set axial position or distance for optimal positioning of vial spike 318 inside vial 12. Once a user has rotated the transport container 210 sufficiently for guide tabs 260 to be seated in end pockets 323, the transport container 210 cannot be rotated and/or axially translated any further, thereby preventing damage to the vial 12 and/or vial spike 318 due to misalignment of the transport container 210 and/or over-insertion of the transport container 210 into docking station 312. At this point, the vial spike 318 has pierced the vial stopper 17 establishing the fluid connection between the vial 12 and the fluid injection system 300, and interface portion 310 is received within distal chamber 234 of first body portion 220.

As shown in FIGS. 26A-26B, the locations for the guide tabs 260 and the guide slots 324 may be reversed. Likewise, the locations guide tabs 260 and the guide slots 256 of the end cap 252 shown in FIG. 21 may also be reversed in the manner shown in FIG. 26B, with respect to guide collar 320.

To remove the transport container 210, a user can rotate the transport container 210 opposite the direction of arrow F of FIG. 26. In this manner, the guide tabs 260 will slide through the helical guide slots 324, such that the transport container 210 is translated axially opposite the direction of arrow E allowing the guide tabs 260 to be withdrawn from guide slot 324 at entrance points 322, thereby allowing the transport container 210 to be completely removed from guide collar 320.

The fluid injection system 300 may also include other features, such as those features described above with respect to fluid injection system 100 at FIGS. 11-12. For example, as illustrated, the guide collar 320 may define one open side 334 for improved visibility during insertion of the transport container 210. Also, the docking station 312 may include a sliding access member (not shown) providing slidable engagement between an open position and a closed position to permit access to receiving chamber 330 containing interface portion 310 and vial spike 318, functioning in substantially the same manner as sliding access member 131 of FIGS. 11-12.

In certain variations of the transport containers 10, 210 and/or fluid/pharmaceutical injection systems 100, 300, wherein the vial 12 is filled with a radiopharmaceutical, the transport containers 10, 210 and/or fluid injection systems 100, 300 could include, for example, an ability to measure the radioactivity of the radiopharmaceutical contained within the vial 12. In one example, measurement may be accomplished by a radiation dosimeter or detector housed within or attached, either separately or integrally, to the transport containers 10, 210, such as in hollow interior cavities 22, 42, 222, 242 of the respective first and second body portions 20, 40, 220, 240. Such a dosimeter may be calibrated for the specific vial 12 used in a specific application and this information may be transmitted via wire or wireless connection to the controller of the fluid injection systems 100, 300.

Another feature, in some embodiments of the transport containers 10, 210 and/or fluid injection systems 100, 300, may be the ability to allow accurate doses of pharmaceutical to be drawn from the vial 12 housed within the transport containers 10, 210. For example, in some embodiments, the transport containers 10, 210 and the fluid injection systems 100, 300 may each include a data storage device for storage and recording of data relating to the pharmaceutical contained within the vial 12, such as the date and time of manufacture and/or preparation, initial radioactivity level, dosimeter calibration curves, container volume, type of pharmaceutical, intended patient, etc. The data storage devices are adapted to be in operative communication, via hardwire connection or wireless connection, with the controller of fluid injection system 100, 300 to communicate the data relating to the pharmaceutical contained in the vial 12 between the transport containers 10, 210 and the controller of the fluid injection systems 100, 300, thereby minimizing user contact. Data may be transferred between the data storage units and fluid injection control system via a number of methods, such as, bar code, radio frequency (RFID), infra-red, Bluetooth, Wi-Fi, etc. The data storage devices may also be in operative communication with the dosimeter, described previously, to record and transfer current data from the dosimeter. Moreover, the data storage devices may interface with the controller of the fluid injection system, such as those disclosed in U.S. Patent Application Publication No. 2011/0178359 to Hirschman et al., which is incorporated herein by reference. Data transferred from the transport containers 10, 210 to the fluid injection systems 100, 300 could then be used by the controller of the fluid injection system to calculate and deliver an accurate dose via the fluid injection systems 100, 300.

In addition, the fluid injection systems 100, 300 may include various mixing devices, containers, and dispensing devices to facilitate the handling, mixing, dispensing, and/or injecting of the pharmaceutical to a patient. For example, the fluid injection mechanism or systems 100, 300 may include a diluent supply, such as saline, and diluent lines to dilute the pharmaceutical. Radiopharmaceuticals generally need to be prepared for injection based on a particular level of radiation. Therefore, the radiopharmaceutical located in the vial 12 may need to be diluted prior to administration to a patient to alter the radiation dose delivered to the patient. This could be accomplished by mixing diluent from the diluent lines with the radiopharmaceutical from the vial 12. This mixing process could be automated by, for example, the controller of the fluid injection system which could control the amount of diluent to be mixed with a dose of pharmaceutical from the vial 12 in the transport containers 10, 210.

While specific embodiments have been described in detail herein, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A pharmaceutical transport container, comprising:
    a first body portion adapted to receive at least a portion of a pharmaceutical vial and defining an opening for establishing fluid communication with the vial, and comprising a proximal end;
    a second body portion engageable with the first body portion to fully enclose the vial, the second body portion having a distal end engageable with the proximal end of the first body portion and a closed proximal end, and defining an interior cavity therebetween; and a flexible ring positioned in the interior cavity of the second body portion and configured to flex between a relaxed state and a radially-outward extended state;

wherein the second body portion is adapted to cooperate with a receiving docking station of a fluid injection system to establish a fluid connection between the vial and a fluid connector element disposed within the docking station as the second body portion is inserted axially into the docking station, and wherein insertion of the first body portion into the interior cavity of the second body portion causes the flexible ring to deform from the relaxed state to the extended state thereby allowing the proximal end of the first body portion to be inserted therethrough, and after such insertion the flexible ring returns to the relaxed state to secure a removable engagement between the first body portion and the second body portion.

2. The pharmaceutical transport container of claim 1, further comprising at least one guide tab extending radially from an exterior surface of the second body portion or within the docking station, the at least one guide tab configured to engage at least one guide slot defined in the exterior surface of the second body portion or defined within the receiving docking station, such that engagement of the at least one guide tab with the at least one guide slot causes the second body portion to translate axially into the docking station to establish the fluid connection between the vial and the fluid connector element disposed within the docking station as a result of the axial translation.

3. The pharmaceutical transport container of claim 2, wherein the at least one guide slot is helical.

4. The pharmaceutical transport container of claim 1, wherein the flexible ring is elliptically-shaped.

5. The pharmaceutical transport container of claim 1, wherein the first body portion comprises a radially-outward extending rim cooperating with the flexible ring to cause a radial deformation of the flexible ring.

6. The pharmaceutical transport container of claim 5, wherein the radially-outward extending rim comprises an outer diameter greater than an inside distance across a minor axis of the flexible ring.

7. The pharmaceutical transport container of claim 1, wherein the first body portion defines a proximally extending wall configured to receive and surround a body of the vial and being receivable within the interior cavity of the second body portion.

8. A pharmaceutical transport container, comprising:
a first body portion adapted to receive at least a portion of a pharmaceutical vial and defining an opening for establishing fluid communication with the vial, and comprising a proximal end;

a second body portion engageable with the first body portion to fully enclose the vial, the second body portion having a distal end engageable with the proximal end of the first body portion and a closed proximal end and defining an interior cavity therebetween; and a flexible ring positioned in the interior cavity of the second body portion and configured to flex between a relaxed state and a radially-outward extended state, wherein insertion of the first body portion into the interior cavity of the second body portion causes the flexible ring to deform from the relaxed state to the extended state thereby allowing the proximal end of the first body portion to be inserted therethrough, and after such insertion the flexible ring returns to the relaxed state to secure a removable engagement between the first body portion and the second body portion.

9. The pharmaceutical transport container of claim 8, further comprising a removable end cap comprising an open proximal end, a closed distal end, and a receiving chamber to receive the first body portion therein to cover the opening and at least one guide tab extending radially from an exterior surface of the second body portion or within the receiving chamber of the end cap, the at least one guide tab engageable within at least one guide slot defined in the exterior surface of the second body portion or within the receiving chamber, the at least one guide slot oriented such that engagement of the at least one guide tab with the at least one guide slot causes the second body portion to translate axially into the receiving chamber of the end cap.

10. The pharmaceutical transport container of claim 9, wherein the at least one guide slot is helical.

11. The pharmaceutical transport container of claim 8, wherein the first body portion defines a hollow interior cavity to accept at least a cap end of the vial.

12. The pharmaceutical transport container of claim 11, wherein the first body portion comprises a radially-inward extending rim in the hollow interior cavity to engage a neck of the vial.

13. The pharmaceutical transport container of claim 8, wherein the second body portion comprises a retaining ring positioned in an interior cavity of the second body portion, the retaining ring maintaining the flexible ring in the interior cavity and abutting a radially-outward extending rim defined on an exterior surface of the first body portion.

14. The pharmaceutical transport container of claim 8, wherein the first body portion is formed as a clamshell movable from an open position to a closed position.

15. The pharmaceutical transport container of claim 8, wherein the first body portion and the second body portion are formed from a radiation-shielding material.

16. A pharmaceutical fluid injection system, comprising:
a pharmaceutical transport container, comprising:
a first body portion adapted to receive at least a portion of a pharmaceutical vial and defining an opening for establishing fluid communication with the vial, and comprising a proximal end;

a second body portion engageable with the first body portion to fully enclose the vial, the second body portion having a distal end engageable with the proximal end of the first body portion and a closed proximal end and defining an interior cavity therebetween;

a flexible ring positioned in the interior cavity of the second body portion and configured to flex between a relaxed state and a radially-outward extended state; and a docking station to axially receive the pharmaceutical transport container therein, the docking station comprising a fluid connector element to establish fluid connection with the vial as the pharmaceutical transport container is received axially into the docking station, wherein insertion of the first body portion into the interior cavity of the second body portion causes the flexible ring to deform from the relaxed state to the extended state thereby allowing the proximal end of the first body portion to be inserted therethrough, and after such insertion the flexible ring returns to the relaxed state to secure a removable engagement between the first body portion and the second body portion.

17. The pharmaceutical fluid injection system of claim 16, further comprising at least one guide tab extending radially from an exterior surface of the second body portion or within the docking station, the at least one guide tab configured to engage at least one guide slot defined in the exterior surface of the second body portion or defined within the receiving docking station, the at least one guide slot oriented such that engagement of the at least one guide tab with the at least one guide slot causes the second body portion to translate axially into the docking station to establish the fluid connection between the vial and a fluid connector element disposed within the docking station as a result of the axial translation.

18. The pharmaceutical fluid injection system of claim 17, wherein the docking station comprises a guide collar, wherein the at least one guide slot is defined in an interior surface of the guide collar.

19. The pharmaceutical fluid injection system of claim 17, wherein the at least one guide slot is helical.

20. The pharmaceutical fluid injection system of claim 16, wherein the fluid connector element comprises a vial spike to puncture a vial stopper at a cap end of the vial.

21. The pharmaceutical injection system of claim 16, wherein the first body portion comprises a radially-outward extending rim cooperating with the flexible ring.

22. The pharmaceutical fluid injection system of claim 21, wherein the radially-outward extending rim is configured to cause a radial deformation of the flexible ring when the first body portion is inserted into the second body portion.

23. The pharmaceutical fluid injection system of claim 21, wherein the radially-outward extending rim comprises an outer diameter greater than an inside distance across the flexible ring.

24. The pharmaceutical fluid injection system of claim 16, wherein the flexible ring is elliptically-shaped.

25. The pharmaceutical fluid injection system of claim 16, wherein the first body portion defines a proximally extending wall configured to receive and surround a body of the vial and being receivable within the interior cavity of the second body portion.

* * * * *

UNITED STATES PATENT AND TRADEMARK OFFICE
CERTIFICATE OF CORRECTION

PATENT NO. : 9,233,776 B2
APPLICATION NO. : 13/800194
DATED : January 12, 2016
INVENTOR(S) : Bazala et al.

It is certified that error appears in the above-identified patent and that said Letters Patent is hereby corrected as shown below:

IN THE SPECIFICATION:
In Column 2, Line 6, delete "radiation shielding" and insert -- radiation-shielding --, therefor.
In Column 14, Line 26, delete "radiation shielding" and insert -- radiation-shielding --, therefor.
In Column 24, Lines 8-9, delete "portion 210," and insert -- portion 220, --, therefor.
In Column 24, Line 54, delete "end 223" and insert -- end 221 --, therefor.

IN THE CLAIMS:
In Column 29, Line 57, in Claim 8, delete "end" and insert -- end, --, therefor.
In Column 30, Line 6, in Claim 9, delete "opening and" and insert -- opening; and --, therefor.
In Column 30, Line 46, in Claim 16, delete "end" and insert -- end, --, therefor.
In Column 30, Line 58, in Claim 16, delete "state" and insert -- state, --, therefor.

Signed and Sealed this
Fourteenth Day of June, 2016

Michelle K. Lee
*Director of the United States Patent and Trademark Office*